(12) United States Patent
Samukawa

(10) Patent No.: US 8,494,783 B2
(45) Date of Patent: Jul. 23, 2013

(54) METHOD AND APPARATUS FOR STORING AND PROCESSING MOLECULAR INFORMATION

(75) Inventor: Hikaru Samukawa, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/350,905

(22) Filed: Jan. 16, 2012

(65) Prior Publication Data

US 2012/0185513 A1 Jul. 19, 2012

Related U.S. Application Data

(60) Continuation of application No. 12/535,430, filed on Aug. 4, 2009, now Pat. No. 8,112,231, which is a division of application No. 10/702,277, filed on Nov. 6, 2003, now abandoned.

(30) Foreign Application Priority Data

Nov. 7, 2002 (JP) ................................. 2002-324310

(51) Int. Cl.
*G01N 33/50* (2006.01)
(52) U.S. Cl.
USPC .......................................................... 702/19
(58) Field of Classification Search
None
See application file for complete search history.

(56) References Cited

U.S. PATENT DOCUMENTS 5,784,294 A 7/1998 Platt et al.
6,223,208 B1 4/2001 Kiefer et al.

OTHER PUBLICATIONS

Tomioka et al., "Green: A program package for docking studies in rational drug design", 1994, Journal of Computer-Aided Molecular Design, vol. 8, pp. 347-366.

*Primary Examiner* — Jason Sims
(74) *Attorney, Agent, or Firm* — William Stock

(57) ABSTRACT

The molecular information providing system of the invention has the terminal units to including molecular structure input/output means, and a molecular information providing apparatus connected via a network to the terminal units and including a database storing a molecular structure, an intermediate representation generated from the molecular structure, and a characteristic decided depending on the molecular structure. The molecular information providing apparatus comprises a coordinate system transforming part for calculating the principal axes of inertia from an atomic arrangement notation specifying the molecular structure, and registering in the database an intermediate representation that is a coordinate transformation of the atomic coordinates into a coordinate system in the directions of the principal axes of inertia, and a retrieval executing part for retrieving the molecular structure stored in the database, employing the intermediate representation.

3 Claims, 18 Drawing Sheets

| | | | |
|---|---:|---:|---:|
| C | 0.00000 | 0.00000 | 1.38667 |
| C | 1.20089 | 0.00000 | 0.69334 |
| C | 1.20089 | 0.00000 | -0.69334 |
| C | 0.00000 | 0.00000 | -1.38667 |
| C | -1.20089 | 0.00000 | -0.69334 |
| C | -1.20089 | 0.00000 | 0.69334 |
| H | 0.00000 | 0.00000 | 2.46925 |
| H | 2.13843 | 0.00000 | 1.23463 |
| H | 2.13843 | 0.00000 | -1.23463 |
| H | 0.00000 | 0.00000 | -2.46925 |
| H | 2.13843 | 0.00000 | -1.23463 |
| H | 2.13843 | 0.00000 | 1.23463 |

FIG. 13

| | | | |
|---|---|---|---|
| C | 0.000 | 0.000 | 1.387 |
| C | 1.201 | 0.000 | 0.693 |
| C | 1.201 | 0.000 | -0.693 |
| C | 0.000 | 0.000 | -1.387 |
| C | -1.201 | 0.000 | -0.693 |
| C | -1.201 | 0.000 | 0.693 |
| H | 0.000 | 0.000 | 2.469 |
| H | 2.138 | 0.000 | 1.235 |
| H | 2.138 | 0.000 | -1.235 |
| H | 0.000 | 0.000 | -2.469 |
| H | -2.138 | 0.000 | -1.235 |
| H | -2.138 | 0.000 | 1.235 |

FIG. 16

METHOD AND APPARATUS FOR STORING AND PROCESSING MOLECULAR INFORMATION

CROSS-REFERENCE TO RELATED APPLICATIONS

This application is a continuation of co-pending U.S. patent application Ser. No. 12/535,430, filed Aug. 4, 2009, which in turn is a divisional application of U.S. patent application Ser. No. 10/702,277, filed Nov. 6, 2003 (now abandoned), which in turn claims the benefit of Japanese patent application number 2002-324310, filed Nov. 7, 2002. All of these applications are herein incorporated by reference in their entireties.

BACKGROUND OF THE INVENTION

1. Field of the Invention

The present invention relates to providing molecular information, and more particularly to a molecular information providing system, a molecular information providing apparatus, a molecular information providing method, a method for controlling an information processing unit as the molecular information providing apparatus, a program for implementing the method in the information processing unit, a mechanically readable storage medium storing the program, and a grid computing support device for computing the molecular orbital, in which the molecular information can be shared by generating an intermediate representation from an atomic arrangement notation to provide high precision information without depending on a format of the atomic arrangement notation from a terminal unit.

2. Description of the Related Art

In recent chemical studies, many designs of molecules having desired characteristics have been made by using computer-aided quantum chemistry calculation to predict characteristics of molecules. In this case, a variety of quantum chemistry computation methods have been well known, including CNDO, CND/S, INDO, MINDO, MINDO3, MINDO5, HF, and RHF, whether empirical or non-empirical, to perform the molecular orbital computation. The above molecular orbital computation includes generating a molecular orbital from an atomic orbital, using an LCAO (Linear Combination of Atomic Orbital) method, wherein an coefficient matrix of eigen-equation having the molecular orbital energy at the diagonal element is transformed into diagonal form, and the molecular orbital as an energy eigenvalue and its corresponding eigenvector are generated by iteration computation. In the above iteration computation, it is well known that the amount of computation is greatly increased as the number of atoms is increased, whereby enormous computer resources such as the CPU occupying time and memory are required.

Examples of a molecular orbital computation software in which the molecular orbital computation is performed employing an empirical or non-empirical method to provide its results to the user may include a MOPAC program package with a semi-empirical computation method, and a GAUSSIAN (trademark) program package (http://www.gaussian.com/) provided by GAUSSIAN company. A molecular orbital program is not limited in terms of the number of atoms in principle, as far as hardware resources are allowable, but a semi-empirical molecular orbital computation method such as MOPAC is applied to the molecules having a relatively great number of atoms, and the analysis object for a non-empirical molecular orbital computation such as GAUSSIAN is often applied to the molecules having a smaller number of atoms due to the limitation of hardware resources. As the molecular orbital computation deals with a smaller number of atoms in the molecule, the same computation for the same molecule is expected to be performed by more users.

For the molecules having a great number of atoms, to which the semi-empirical molecular orbital computation such as MOPAC is mainly performed conventionally, there is the possibility that a molecule having a specific feature is computed at any site, and the knowledge about the desired characteristic of the molecule is possibly accumulated with any computer in the world, although not publicized.

Accordingly, if the computation result obtained using the molecular orbital computation such as GAUSSIAN or MOPAC is accumulated in a common database, it is possible to input the molecular structure and retrieve the data having the same molecular structure as the input molecular structure from the database rapidly and accurately. By employing the above database, it is possible to provide the more accurate result more rapidly than making the computation using the limited computer resources at each terminal computer. Accordingly, if the analysis results of the molecular orbital computation are shared, the computer resources are saved and the computation cost is reduced, making it possible to acquire promptly the information such as the molecular structure and electron structure by molecular orbital computation, reactivity, effect of medicine, side reaction, and electrical, electronic or optical characteristic. Besides the molecular orbital method, if the molecular data having the characteristics associated with the molecular structure such as material design or analysis are shared and retrieved at high precision, the labor of the user is reduced.

Further, there is a greater advantage of sharing the information of the database when more users gain access to the database, typically in the environment of grid computing. For example, it is said that half or more of the computation jobs by the users all over the world to make the molecular orbital computation employing a GAUSSIAN program package are substantially duplicated. Therefore, it is preferable to share the computation results already obtained to achieve more effective use of the computer resources.

In the computation regarding the shape or structure, there is a method for computing the shape in terms of a sequence of points in the field of computer graphics, in addition to the computational chemistry (molecular orbital method), in which this method may be applied to the computation of molecule. However, the atoms making up the sequence of points in the computational chemistry contain the atomic attribute called an atomic number (atomic weight), besides the positional information, causing another problem. For example, even if the molecules have no proximate root (asymmetry) in the shape, the proximate multiple root may be recognized in the moment of inertia, irrespective of asymmetry in the shape, when the moment of inertia is computed from the molecule structure. In the computational chemistry, the atomic number is an important value representing the bond between elements, and it is not appropriate to arbitrarily change the atomic number for the structure comparison.

In the molecular orbital method, the molecular structure is denoted employing an atomic arrangement notation as the general representation of atomic arrangement, for example, H6C6 for benzene, in which the combinations of atomic symbol and number of atoms are arranged in the order of atomic number. Accordingly, it is needed to find the molecule having the same atomic arrangement notation and the consistent molecular structure from the database to make a comparison between the molecular structures for use in the molecular orbital computation. More specifically, it is necessary to compare the coordinate values of each atom in the molecules with the same atomic arrangement notation. However, it is often meaningless to compare the coordinate values themselves, because the representation method of the molecular structure has various input formats or coordinate systems and a limited number of significant digits. The user acquires the positional coordinates of atoms making up the molecule by various methods, then transforms them into a proper coordinate system employed by the user, a Cartesian coordinate system in most cases, or the atomic arrangement notation in a Z matrix format as will be described later, to make the computation by the molecular orbital method. Therefore, it is required to transform the molecular structure into a representation system (uniquely decided from the physical properties of the molecular structure) that is not dependent on the input format or coordinate system employed by the user.

In the molecular orbital method described above, there is an attempt for avoiding duplication of the molecular orbital computation for the molecules which have been already dealt with for analysis computation by comparing the input data specifying the molecular structure and the molecular structure data accumulated in the database and giving the analysis result. More specifically, the computation data is input in the interactive way, and the comparison of molecular structure is made between the input data of molecular structure input on the text basis and the positional coordinates on the text basis registered in the database by determining whether or not they are coincident in the text level.

Though the above retrieval method is well known, the computation result obtained by the molecular orbital method has many kinds of parameters and various combinations of them. When the residuals of coordinates of atom in the molecular structure are calculated sequentially on the text basis to identify the molecule as a sum of residuals, a determination is made employing the total of input positional deviations. Hence, when a plurality of candidate molecules with the same amount of positional deviations are selected, it is required to make a determination of which structure to select, including a round-off error in the computer. Therefore, the retrieved result may be graphically presented to the user for determination. However, if the user makes a determination graphically, a problem arises that the precision of selection is degraded, and there is some uncertainty in selection. Therefore, when the molecular orbital computation was made by grid computing, there was a need for a packaging method for comparing the molecular structures using a representation system more clearly reflecting the molecular structure than comparing them sequentially on the text basis to simplify the understandings of the molecular structure, and provide the information promptly and precisely.

SUMMARY OF THE INVENTION

This invention has been achieved in the light of the above-mentioned problems associated with the prior art, and has a concept that the molecular information is provided promptly and precisely if the molecular structure is retrieved under the common criteria and with a round-off error, employing an input format of molecular structure, and a transformation into a representation system directly reflecting the molecular structure, in which there is no need that the user specifies the input format of molecular structure. Moreover, if the representation system is applied for the grid computing, the results of the molecular orbital computation can be shared among the users conveniently, promptly and precisely.

In a specific embodiment of the invention, the entire molecule for retrieval is regarded as one rigid body, and its center of gravity, a principal moment of inertia around the center of gravity, and the directions of the principal axes of inertia are calculated by solving a characteristic equation based on the input format input by the user. The coordinate values of atom is transformed into an intermediate representation generated from the coordinate values as seen in a coordinate system decided from the calculated principal axes of inertia, and the retrieval is performed by comparing the intermediate representations. The molecular structures are compared by comparing the positional coordinates between atoms, after transformation into the intermediate representation, without depending on the input format of the coordinate system input by the user.

Moreover, in comparing the molecular structures using the intermediate representation in this invention, a process for appending three different principal moments of inertia (hereinafter referred to as the "eigenvalue" in this specification) to the molecule is performed for highly precise comparison. The above process is referred to as the proximate eigenvalue handling process in this invention. Through the proximate eigenvalue handling process, less degenerate or proximate eigenvalue can be given to the molecule for which it is determined that at least two principal moments of inertia degenerate or artificially degenerate, specifically, at least two eigenvalues has the same value (multiple root) or proximate values, for example, in the case where the molecule is highly symmetrical and has a plane of reflection sh or sv, and the axis of symmetry Cn. Through this process, the coordinate system is uniquely decided for the molecule having intrinsically degenerate or proximate eigenvalue without arbitrariness in the directions of the principal axes of inertia. Also, it is possible to resolve the disadvantage that when there is a proximate eigenvalue but not the multiple root, the precision in the directions of the principal axes of inertia is degraded to bring about some uncertainty in determining whether or not the coordinate values are consistent, resulting in less sufficient precision or certainty for designating or retrieving the molecular structure.

The proximate eigenvalue handling process generates an intermediate representation for retrieval by changing the predetermined atomic attribute in the input data of the molecular structure. This intermediate representation has the same point sequence structure and symmetry as the input molecular structure, but is generated so that the eigenvalue in the inertial matrix (i.e., principal moment of inertia) may not be the proximate or multiple root. In this invention, the unique coordinate system is assured, employing the intermediate representation with the broken symmetry of molecule, and the stabilization, high reliability and high precision of the provided molecular information can be realized.

That is, according to this invention, there is provided a molecular information providing system having a terminal unit including molecular structure input/output means, and a molecular information providing apparatus connected via a network to the terminal unit and including a database storing a molecular structure, an intermediate representation generated from the molecular structure, and a characteristic decided depending on the molecular structure, the molecular information providing apparatus comprising means for calculating the principal axes of inertia from an atomic arrangement notation specifying the molecular structure, and registering in the database an intermediate representation that is a coordinate transformation of the atomic coordinates into a coordinate system in the directions of the principal axes of inertia, and means for retrieving the molecular structure stored in the database, employing the intermediate representation.

In this invention, the means for calculating the principal axes of inertia may comprise means for changing the atomic attribute of atoms making up the remotest pair in the molecular structure and the atomic attribute of an atom farthest away from the remotest pair.

In this invention, the molecular information providing system may further comprise means for making an origin of coordinates in the intermediate representation coincide with a center of gravity decided employing the changed atomic attribute.

In this invention, a molecular information providing system according to Claim 1 is provided wherein the characteristic decided depending on the molecular structure may be an electronic, electrical or optical characteristic of a molecule.

In this invention, the molecular information providing apparatus may comprise means for determining the proximity of a moment of inertia to the principal axes of inertia.

According to this invention, there is provided a molecular information providing apparatus for retrieving a characteristic decided depending on a molecular structure stored in a database, on the basis of the molecular structure, the molecular information providing apparatus comprising means for calculating the principal axes of inertia from an atomic arrangement notation specifying the molecular structure, and registering in the database an intermediate representation that is a coordinate transformation of the atomic coordinates into a coordinate system in the directions of the principal axes of inertia, and means for retrieving the molecular structure stored in the database, employing the intermediate representation.

According to this invention, there is provided a method for controlling a molecular information providing apparatus that is an information processing unit including a database for retrieving a characteristic decided depending on a molecular structure on the basis of the molecular structure, the method comprising a step of calculating the principal axes of inertia from an atomic arrangement notation specifying the molecular structure, and registering the principal axes of inertia in a memory, a step of determining the proximity of a moment of inertia to the principal axes of inertia, a step of reading out data of the principal axes of inertia from the memory, and registering in the database an intermediate representation that is a coordinate transformation of the atomic coordinates into a coordinate system in the directions of the principal axes of inertia, and a step of retrieving the molecular structure stored in the database, employing the intermediate representation, and registering the retrieved molecular structure in the memory.

In this invention, the step of calculating and registering the principal axes of inertia in the memory may comprise a step of changing the atomic attribute of atoms making up the remotest pair in the molecular structure and the atomic attribute of an atom farthest away from the remotest pair.

In this invention, the method may further comprise a step of calculating a characteristic decided depending on the molecular structure, wherein the characteristic is an electronic, electrical or optical characteristic of a molecule that is given by a molecular orbital computation.

According to this invention, there is provided a program for implementing a method for controlling a molecular information providing apparatus that is an information processing unit including a database for retrieving a characteristic decided depending on a molecular structure on the basis of the molecular structure, the program being executed by the information processing unit, the method comprising a step of calculating the principal axes of inertia from an atomic arrangement notation specifying the molecular structure, and registering the principal axes of inertia in a memory, a step of determining the proximity of a moment of inertia to the principal axes of inertia, a step of reading out data of the principal axes of inertia from the memory, and registering in the database an intermediate representation that is a coordinate transformation of the atomic coordinates into a coordinate system in the direction of the principal axes of inertia, and a step of retrieving the molecular structure stored in the database, employing the intermediate representation, and registering the retrieved molecular structure in the memory.

According to this invention, there is provided a mechanically readable storage medium storing a program for implementing a method for controlling a molecular information providing apparatus that is an information processing unit including a database for retrieving a characteristic decided depending on a molecular structure on the basis of the molecular structure, the program being executed by the information processing unit, the method comprising a step of calculating the principal axes of inertia from an atomic arrangement notation specifying the molecular structure, and registering the principal axes of inertia in a memory, a step of determining the proximity of a moment of inertia to the principal axes of inertia, a step of reading out data of the principal axes of inertia from the memory, and registering in the database an intermediate representation that is a coordinate transformation of the atomic coordinates into a coordinate system in the directions of the principal axes of inertia, and a step of retrieving the molecular structure stored in the database, employing the intermediate representation, and registering the retrieved molecular structure in the memory.

According to this invention, there is provided a grid computing support device for supporting a grid computing environment for molecular orbital computation connected via a network, the support device comprising means for calculating the principal axes of inertia from an atomic arrangement notation specifying the molecular structure, means for making the molecular orbital computation, employing the atomic arrangement notation, means for registering in the database an intermediate representation of the atomic arrangement notation that is a coordinate transformation of the atomic coordinates into a coordinate system in the directions of the principal axes of inertia, associated with a characteristic generated by the intermediate representation and the molecular orbital computation, and means for retrieving the molecular structure stored in the database, employing the intermediate representation.

In this invention, the grid computing support device may further comprise means for transmitting the retrieved molecular structure, along with a judgment criterion acquired from the intermediate representation, via a network.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 12 shows the atomic arrangement notation of benzene in the Z matrix format as shown in FIG. 11;

FIG. 13 shows the atomic arrangement notation of benzene in a Cartesian format as shown in FIG. 11;

FIG. 16 shows the atomic arrangement notation of benzene with different effective digits;

DETAILED DESCRIPTION OF THE PREFERRED EMBODIMENT

A method of the present invention is especially effective to be applied to the non-linear molecules having primarily four or more atoms. Its reason is that the molecule having three or less atoms can be simply determined by comparing the distances between atoms, and the linear molecule can be specified by the interatomic distance, the remotest pair and the nearest pair. This invention is applicable to the fields of employing various analytical data with the molecular structure as a retrieval key, such as the retrieval for various characteristics related to the molecular structure, for example, retrieval for the analysis result of the molecular orbital computation, material design, medicine design, molecule identification, absorption spectrum estimation, and dipole moment estimation. In the following, this invention will be specifically described in connection with the preferred embodiments in the field where the analysis result of the molecular orbital computation is retrieved from the molecular structure in this specification.

Figure 1:
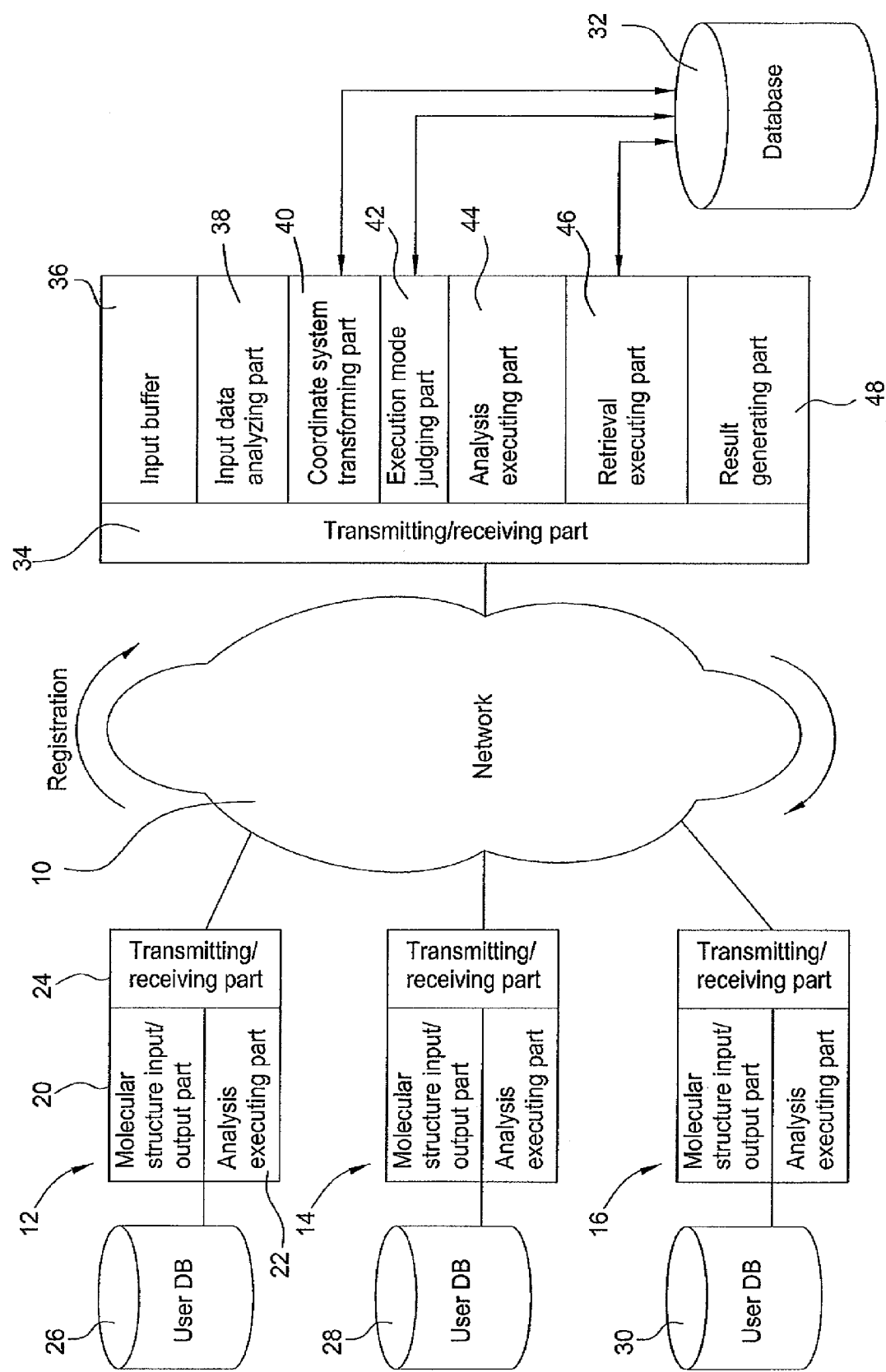
FIG. 1 is a block diagram of a molecular information providing system according to a first embodiment of the present invention.

FIG. 1 is a schematic block diagram of a molecular information providing system according to a first embodiment of the invention. The molecular information providing system as shown in FIG. 1 is composed of the terminal units 12 to 16 which are interconnected via a network 10, and a molecular information providing apparatus 18 for receiving input data including the atomic arrangement notation of a molecule from the terminal units 12 to 16, and receiving the analysis result of the molecule by the molecular orbital computation via the network, in which the molecular information providing apparatus may perform the molecular orbital computation, as needed.

Each of the terminal units 12 to 16 transmits a retrieval request to the molecular information providing apparatus 18, and receives the retrieved result in response to the request along with the molecular data and the judgment criterion (coincidence criterion). In the embodiment as shown in FIG. 1, each of the terminal units 12 to 16 can perform the molecular orbital computation by itself, and transmit the retrieved result to the molecular information providing apparatus 18 to register it in a database to share the information. Also, the molecular information providing apparatus 18 executes a molecular orbital computation job or retrieval job requested from the terminal units 12 to 16, and returns its result to a terminal unit that has issued the request to enable the sharing of information. The terminal unit and the molecular information providing apparatus according to the invention will be described below in more detail.

<Terminal Unit>

The terminal units 12 to 16 of the invention consist of information processing means such as a workstation, a general-purpose large computer, or a personal computer. The information processing means may be configured in various different forms in accordance with the user's needs, but at least comprises a molecular structure input/output part 20, an analysis executing part 22, and a transmitting/receiving part 24 for transmitting the analysis result to the molecular information providing apparatus 18 and receiving the computed or retrieved result of the molecular information providing apparatus 18, as shown in FIG. 1. The number of terminal units usable in this invention is not particularly limited, but is permissible up to the number of users who want to receive the provided information. More specifically, the terminal units 12 to 16 may be installed at the computer center or computer department of a college, a research installation or a company's institute.

The molecular structure input/output part 20 comprises a hard printer, a CRT, and a liquid crystal display unit. For example, the user inputs graphically a molecular structure, whereby the atom coordinates at the position of atom on the CRT are transformed into the Cartesian coordinate or Z matrix format to provide the data for the molecular orbital computation or retrieval which is requested to the molecular information providing apparatus 18. Moreover, the terminal units 12 to 16 are connected to the user databases (user DBs) 26 to 30, respectively, to store the computation result obtained in the past by the terminal units or the analysis result transmitted from the molecular information providing apparatus 18.

Also, the terminal units 12 to 16 comprise the molecular structure input means in the molecular structure input part 20. The user constructs a desired molecular structure on the terminal units 12 to 16, employing an appropriate graphical user interface. This graphical user interface preferably has a function of creating a primary structure by selecting the atoms and arranging them on the display screen by designating the bonding between atoms, and creating a secondary structure by optimizing the structure by a simple molecular dynamic method to perform the analysis and retrieval at higher precision. Moreover, according to another embodiment of the invention, the created primary structure is read into the analysis executing part 22 in the terminal unit, and optimized, employing a semi-empirical method such as CNDO, INDO or MNDO with relatively less consumption of hardware resources than a non-empirical computation method such as Ab-initio computation, whereby the more precise molecular structure is given by the atomic arrangement notation in the Cartesian format or Z matrix format. In the case where the terminal unit 12 to 16 has a means or device that allows the user to experimentally decide the molecular structure at high precision, the experimental data may be directly input into the graphical user interface, and transformed into the atomic arrangement notation in the Cartesian format or Z matrix format, and the input data including the obtained atomic arrangement notation may be transmitted to the molecular information providing apparatus 18. In any case, the user at the terminal unit describes the molecular structure, employing the accustomed atomic arrangement notation, and acquires the information for the atomic arrangement notation from the molecular information providing apparatus.

<Molecular Information Providing Apparatus>

The molecular information providing apparatus 18 comprises a high speed information processing unit such as a workstation, a so-called super computer, or a general-purpose computer, in which the past computation result stored in a database 32 is retrieved, employing the information transmitted from the terminal unit, and if the past analysis result is found, the information is transmitted to the terminal unit 12 to 16. Also, the molecular information providing apparatus 18 may transmit, to the terminal unit 12 to 16, a computation method designated by the user and the intended characteristic by computing it, if the estimated computation time is shorter than a predetermined threshold value. Also, the molecular information providing apparatus 18 accumulates the newly analyzed result in the database 32.

In the molecular information providing apparatus 18, the analysis result of molecule that is already analyzed, the analysis parameters such as the base function, spin multiplicity and electric charges, and other parameters such as the intermediate representation, the remotest pair and the nearest pair, which are given by the atomic arrangement notation employing the principal axes of inertia in the molecular structure, are registered as a set of data, whereby the transmitting/receiving part 34 can exchange the data with the terminal unit 12 to 16 remotely connected via the network 10. The molecular information providing apparatus 18 according to the first embodiment of the invention updates the accumulated analysis result as the shared information to the terminal units 12 to 16 periodically or as requested.

Figure 2:
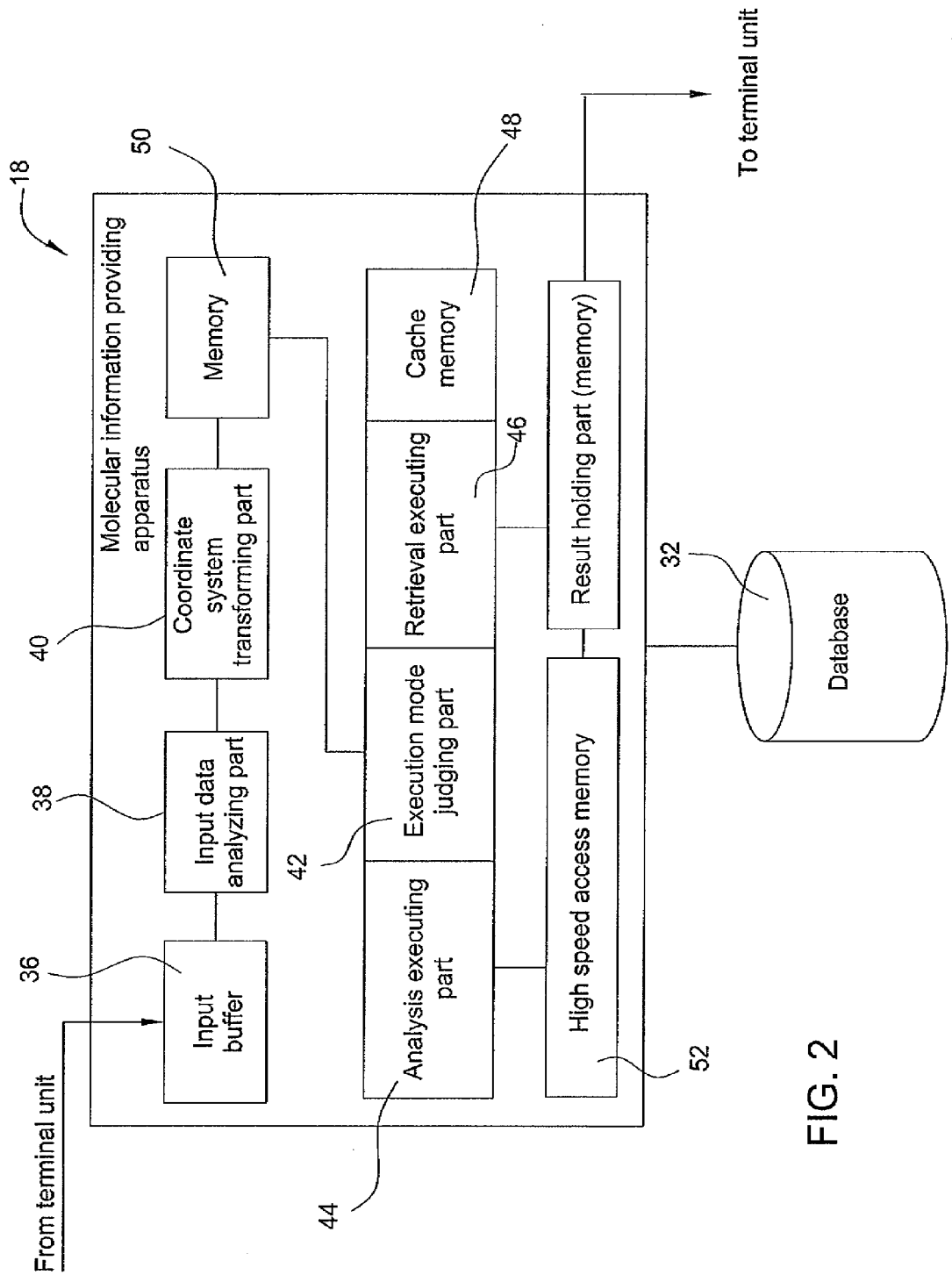
FIG. 2 is a schematic block diagram showing the functions of a molecular information providing apparatus according to the invention.

FIG. 2 is a schematic block diagram showing the functional blocks of the molecular information providing apparatus according to the invention. The molecular information providing apparatus 18 comprises an input buffer 36, an input file analyzing part 38, a coordinate system transforming part 40, and an execution time estimating part 42. The molecular information providing apparatus 18 receives from the terminal unit 12 to 16 the input data including the atomic arrangement notation, a designation of the method of molecular orbital computation, the base function, and the parameters necessary for the analysis, and stores the received information in the input buffer 36. The input data such as the atomic arrangement notation stored in the input buffer 36 is read into the input file analyzing part 38, in which the atomic arrangement notation format employed by the user is firstly determined.

Also, the input file analyzing part 38 acquires, from the data read out from the input buffer 36, the designation of the method of molecular orbital computation, the base function and the parameters necessary for the analysis. If the atomic arrangement notation format is determined in the input file analyzing part 38, the acquired atomic arrangement notation is passed to a coordinate system transforming part 40, and transformed into an appropriate format, e.g., Cartesian format, that is employed by the molecular information providing apparatus 18. At the same time, an inertial matrix is created, employing the received atomic arrangement notation, the eigenvalue computation is performed to calculate the principal axes of inertia, and the position of atom is projected onto the principal axes of inertia to generate the intermediate representation of the molecular structure from the coordinates as seen from the principal axes of inertia. Thereafter, the execution mode judging part 42 selects an analysis and retrieval process by the molecular orbital method, based on the analysis data obtained, in accordance with the time required for the analysis, thereby providing most efficiently the molecular information.

As shown in FIG. 2, the molecular information providing apparatus 18 comprises an analysis executing part 44 for executing the molecular orbital computation, a retrieval executing part 46 for retrieving the analysis result accumulated, and a result holding part 48. The analysis executing part 44 executes the analysis by the molecular orbital method if the estimated execution time in the execution mode judging part 42 is smaller than a preset threshold value, and if there is no analysis result under the designated conditions for the molecule of retrieval object. On the other hand, if the estimated execution time in the execution mode judging part 42 is longer than the threshold value, the retrieving part 46 performs the retrieval for the database 32, employing the data of the intermediate representation, the remotest pair and the nearest pair, to prevent wasteful execution of analysis computation. By retrieval, if the result of analysis computation under the already designated conditions is stored in the database 32, the data is read out from the database 32 and stored in the result holding part 48 comprising a cache memory.

As a result of retrieval, if the relevant analysis result is not found, the analysis executing part 44 executes the molecular orbital computation, whereby the analysis result, along with the intermediate representation, the remotest pair and the nearest pair, is stored in the database 32 and utilized upon an analysis request that will be issued later. At the same time, the analysis result is stored in the result holding part 48, and the stored result is downloaded to the user. In the above manner, the analysis result newly produced employing the information received from a plurality of terminal units is accumulated in the database 32. In the first embodiment of the invention, the accumulated analysis result is updated as the shared information to the terminal units 12 to 16 after the elapse of a fixed period of time or a certain amount of the analysis result is accumulated, whereby the data accumulated in the user DBs 26 to 30 is updated.

Figure 3:
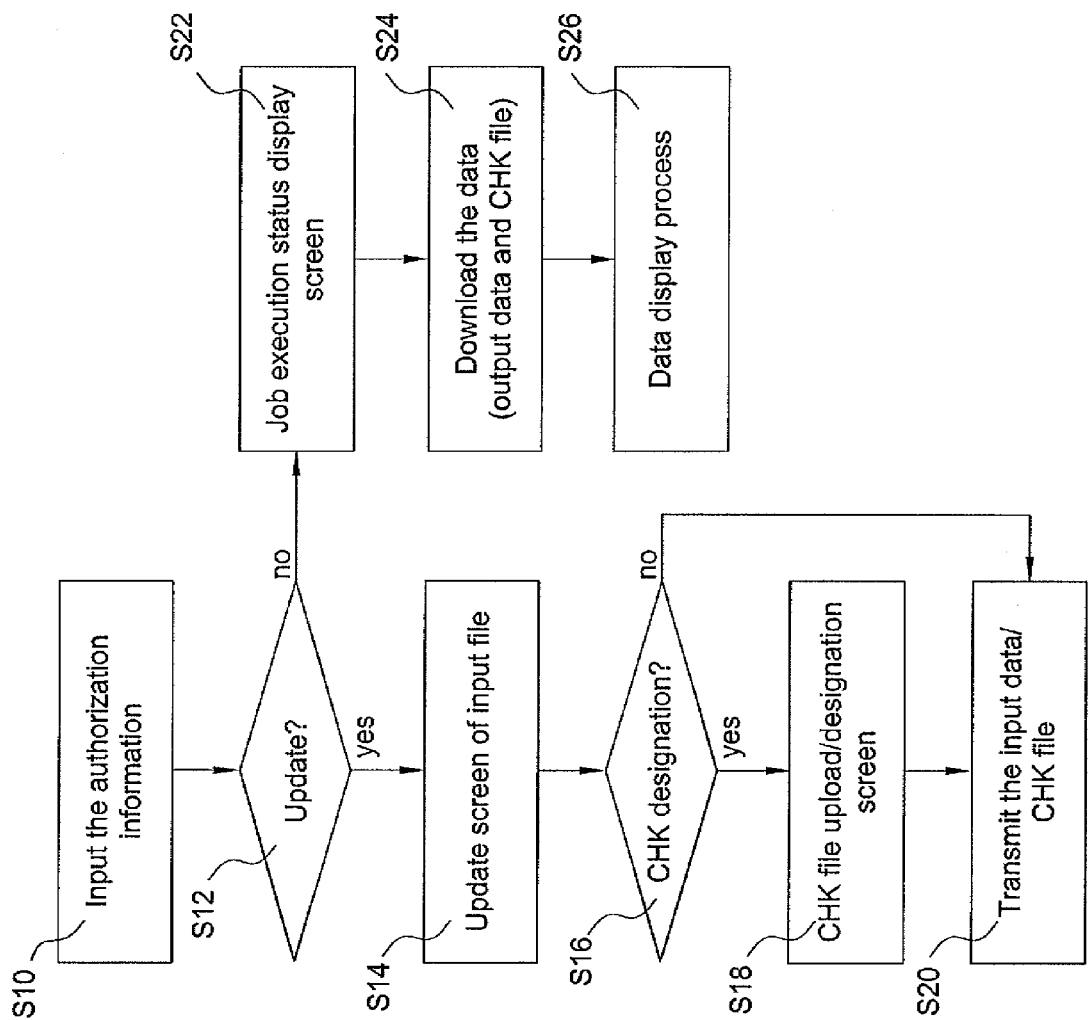
FIG. 3 is a flowchart showing a process performed by a terminal unit of the invention.

FIG. 3 is a flowchart showing a process performed by the terminal unit of the invention. In the terminal unit of the invention, at step S10, a secret key and a public key given for each terminal unit are input to authorize the user to receive the molecular information provided from the molecular information providing apparatus 8. The secret key and the public key may be encrypted, employing an appropriate encryption method, to protect the molecular information providing apparatus 18 from the improper access. After inputting the authorization information in the terminal unit, at step S12, a screen is displayed for the user of the terminal to select a processing of updating a new atomic arrangement notation or determining a job execution status of the molecular orbital computation already instructed.

If the user acquires the molecular information with the new atomic arrangement notation updated (yes), the procedure proceeds to step S14, where an update screen for updating the input file containing the atomic arrangement notation for the molecular information providing apparatus 18 is displayed to the user. At step S16, the user selects whether or not to specify a check point file (hereinafter referred to as a CHK file) holding the intermediate data concerning the progress of job, and if so (yes), a CHK file uploading/specifying screen is displayed to the user at step S18. If the CHK file is not specified (no) at step S16, and if the CHK file is specified at step S18, the input data and the CHK file are transmitted to the molecular information providing apparatus at step S20.

On the other hand, if uploading the input data is not selected (no) at step S12, for example, when a job request is already made to the molecular structure providing apparatus, the procedure branches to step S22, where the job status display screen is presented to the user. At step S24, the already computed analysis result (output data and CHK file) or the retrieved result is downloaded. At step S26, the downloaded data is displayed by, for example, activating the graphical user interface.

Figure 4:
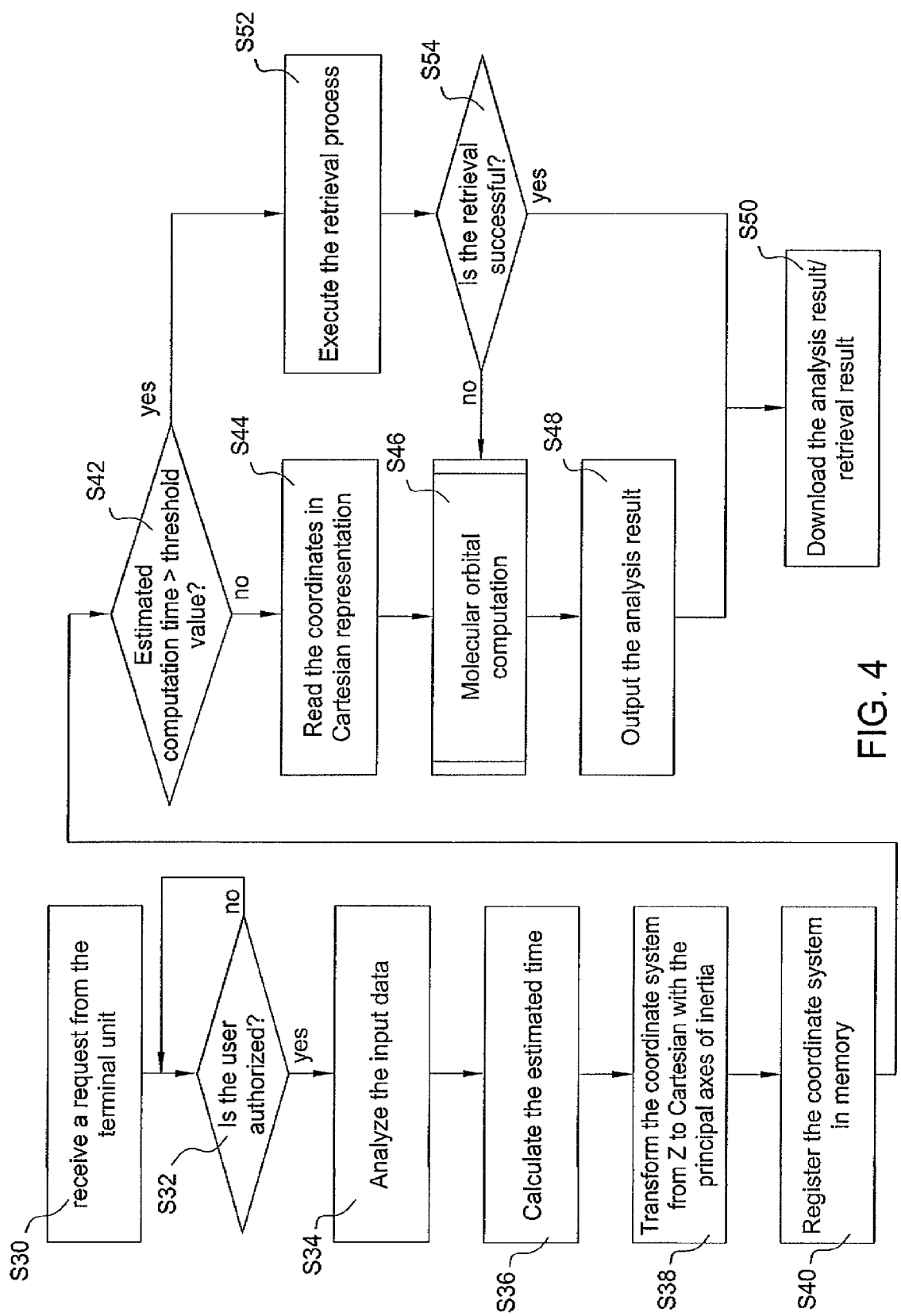
FIG. 4 is a flowchart showing a process performed by the molecular information providing apparatus according to the invention.

FIG. 4 is a flowchart showing a process performed by the molecular information providing apparatus 18 according to the invention. At step S30, the molecular information providing apparatus of the invention receives as a packet the data including a processing request, the input data and the user information from the terminal unit via the network. At step S32, a determination is made whether the user is authorized by extracting the authorization information from the received packet. If the user is authorized (yes), the remaining data included in the input data is analyzed at step S34, thereby acquiring the information used for the analysis computation including a computation method such as CSMM (electric charges, spin multiplicity, chemical formula), MNDO, CNDO, INDO, HF, RFF or CI (Configuration Interaction), a base function such as STO-3G, 4-31G or 4-31G, and a job type. At step S36, the estimated computation time is computed. If the user authorization is not made (no) at step S32**, the user is informed that the user authorization is not made after a predetermined number of retries.

Then, the atomic arrangement notation is extracted from the input data. At step S38, the format of atomic arrangement notation employed by the user is analyzed, and if an analysis software package is GAUSSIAN, the coordinate system is transformed from the Z matrix format into the Cartesian format. At the same time, the inertial matrix is created from the atomic arrangement notation sent from the user to calculate the eigenvalue and the eigenvector and decide the principal axes of inertia. If the principal axes of inertia are decided, the coordinate values of atom acquired from the atomic arrangement notation are projected onto the principal axes of inertia to generate the intermediate representation from the positional coordinate data of atom as seen from the principal axes of inertia. At step S40, the generated atomic arrangement notation and the intermediate representation are registered in the memory. At step S42, a determination is made whether or not the estimated computation time is longer than a threshold value. In this case, the threshold value may be a mean value of the retrieval execution time that is monitored, because the molecule is small and the base function and the computation method itself do not involve the use of a lot of hardware resources.

At step S42, if the estimated computation time is fully shorter (no), the atomic arrangement notation in the Cartesian format is read out from the memory at step S44, and the molecular orbital computation is performed employing a designated method and the base function at step S46. At step S48, the analysis result is output to the memory at the end of the analysis computation. At step S50, the analysis result is downloaded from the memory to the terminal unit via the network. Also, if the estimated computation time is greater than or equal to the threshold value (yes), the procedure proceeds to step S52 to perform the retrieval process, whereby the screening is made employing the remotest pair and the nearest pair generated from the input data, and the high precision retrieval is made by comparing the intermediate representation transformed from the input data and the intermediate representation read out from the database.

If the analysis result with the intermediate representation adapted is registered in the database (yes), the retrieved result with the coincidence criterion is registered in the memory, and downloaded to the terminal unit at step S50. Also, if the matched intermediate representation is not registered in the database (no), the procedure returns to step S46 to perform the molecular orbital computation, whereby a new analysis result is generated, and registered in the memory. Then, the new analysis result is provided to the user at step S50. At the same time, the analysis result, together with the data including the intermediate representation, the computation method, the base function, electric charge information, and the spin multiplicity, is registered in the database, whereby the new analysis result is shared.

Figure 5:
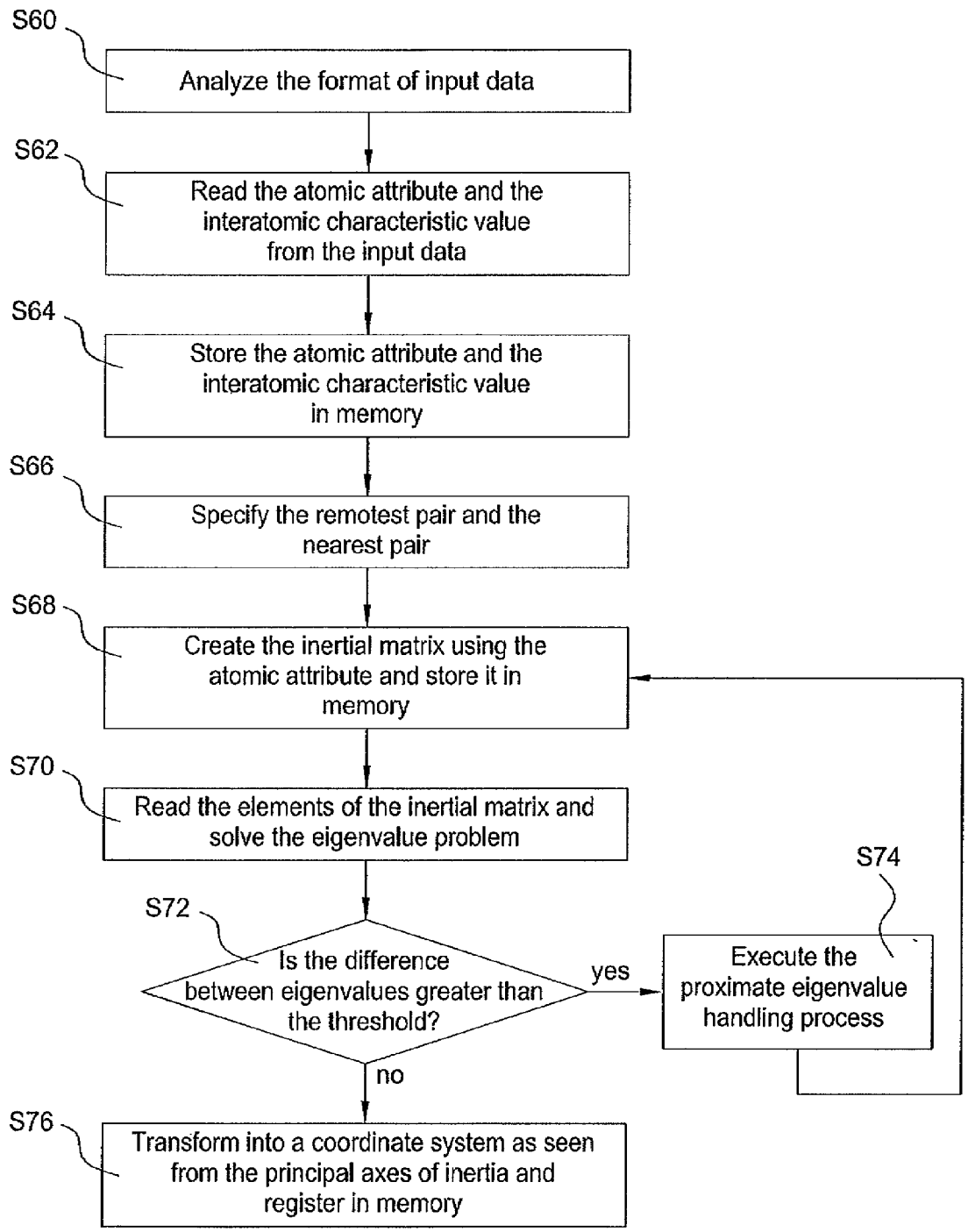
FIG. 5 is a flowchart showing a process for generating an intermediate representation of a molecular structure according to the invention.

FIG. 5 is a flowchart showing the details of a coordinate system transformation process at step S38 in the procedure of the invention. The coordinate system transformation process of this invention analyzes the format of atomic arrangement notation contained in the received packet at step S60. If the format is judged, the atomic attribute such as the atomic number and the interatomic characteristic values such as the interatomic distance and the dihedral angle are read out at step S62, and stored in the memory at step S64. At step S66, the interatomic characteristic values are read out from the memory to specify the remotest pair and the nearest pair, and at the same time to calculate the distance between them, which is then registered in the memory. At step S68, the inertial matrix is created, employing the atomic attribute and the interatomic characteristic values, and registered in the memory. At step S70, each element of the inertial matrix is read out, whereby the eigenvalue is calculated and registered in the memory by solving an eigenvalue problem.

At step S72, a determination is made whether or not a difference between eigenvalues is greater than a predetermined threshold value, and if the difference for at least two eigenvalues is smaller than or equal to the threshold value (yes), the procedure proceeds to step S74 to perform a proximate eigenvalue handling process, because the eigenvalues are quite proximate, whether multiple root or not, to bring about some uncertainty in deciding the principal axes of inertia. In the proximate eigenvalue handling process, the atomic attribute is changed so that at least two eigenvalues are not multiple or proximate root. Thereafter, its result is input at step S68 to calculate the inertial matrix again and solve the eigenvalue problem. Then, at step S70, the eigenvalue for the intermediate representation is calculated. Since for this intermediate representation, the atomic attribute is changed according to a certain rule so that the proximate eigenvalues are not produced, the determination is inevitably negative (no) at step S72 in the next loop. At step S76, the eigenvectors corresponding to the eigenvalues are sorted in the smaller order to decide the principal axes of inertia. Then, the position of atom is transformed into the coordinate system as seen from the principal axes of inertia, whereby the atomic coordinates in the intermediate representation are generated and registered in the memory. The above coordinate system transformation process of the invention is made by changing the atomic attribute, or particularly the atomic number (mass), of atom at the position selected according to a certain rule so that no multiple root is produced in the eigenvalue computation for the inertial matrix of the highly symmetrical molecule.

More specifically, if the atom selected according to the certain rule is H (hydrogen atom), the atomic weight of atom at that position is increased by integral times, or eight times in the specific embodiment, and replaced with a virtual atom 8H to continue the computation. In this case, the atomic weight is only numerically changed, and other characteristics such as the dihedral angle and the interatomic distance are preserved to keep the structure given by the atomic arrangement notation, whereby it is possible to most effectively eliminate any uncertainty in selecting the principal axes of inertia corresponding to the proximate eigenvalues without changing the structure. Also, the data with the changed atomic attribute is input at step S68, whereby the atomic coordinates given by the atomic arrangement notation and the center of gravity obtained by the atomic attribute are unchanged, and the origin of the principal axes of inertia, namely, the origin of the intermediate representation is kept coincident with the center of gravity of the molecule. In this invention, for the molecule with the atomic arrangement notation registered in the database, the intermediate representation and its analysis result are paired or linked and stored, whereby the retrieval for the molecule and the analysis result can be performed, based on the comparison between the intermediate representations.

The details of the proximate eigenvalue handling process according to the embodiment of the invention will be now described.

(1) Calculation of Interatomic Distance

The distance between two atoms is computed to acquire the distance of the remotest pair and the distance of the nearest pair. The distance of the remotest pair may be added to the data in the database and employed for a judgment to promptly exclude the molecule with inconsistent molecular structure from a number of registered molecules. Also, the distance of the remotest pair and the distance of the nearest pair may be returned to the user as the reference values when the user finally makes a determination whether the structure is consistent or not.

(2) Eigenvalue Problem

Mass of atom is related with the atomic number, and the most general approach in the computation chemistry. The "center of gravity" as used herein means the "charge center of nucleus" of a molecule. It is supposed that the "directions of principal axes of inertia" coincide with the "standard conformation". Also, in this invention, the entire molecule is regarded as a rigid body, whereby the center of gravity, the principal moment of inertia around the center of gravity, and the directions of the principal axes of inertia are computed. More specifically, this computation is grasped as an eigenvalue problem with the coefficients being the elements of a 3'3 inertial matrix which has a moment of inertia at diagonal elements and a product of inertia at non-diagonal elements in a given coordinate system. In this invention, the principal moments of inertia are computed as the eigenvalues and the principal axes of inertia as the eigenvectors by transforming the 3'3 matrix into a diagonal matrix. The acquired eigenvalues are supposed to be I1, I2 and I3 in the smaller order and the corresponding eigenvectors are v1, v2 and v3. To judge that I1, I2 and I3 are separated, it is assumed that a relative error between the moments of inertia is 0.1% or more in view of a round-off error.

(3) Proximate Eigenvalue Handling Process

If there are any proximate roots in three roots, first of all, the mass of atom selected as the remotest pair is increased or decreased while preserving the characteristic values such as the interatomic distance and the dihedral angle. Typically, it is preferable that the mass is increased, because hydrogen atom is mostly selected. Though the way of increasing the mass is particularly not limited, the masses of atoms making up the remotest pair may be increased by integral times (e.g., eight times) in the specific embodiment of the invention. At the same time, a line connecting the remotest pair is calculated, and the mass of the atom located at the largest distance from this line (hereinafter referred to as "atom farthest away from the remotest pair") is increased by integral times (e.g., four times), whereby the inertial matrix is updated, and the eignevalue computation is performed to obtain three different eigenvalues I4, I5 and I6 and the corresponding eigenvectors v4, v5 and v6. The updating computation of the inertia matrix is made by using the data of eigenvalue computation already computed and held in the memory, except for data regarding the remotest pair and the atom farthest away from the remotest pair. Accordingly, in the proximate eigenvalue handling process of this invention, it is only necessary to process the changed part for three atoms of the remotest pair and the atom farthest away from the remotest pair. Therefore, the proximate eigenvalue handling process of the invention is performed, without the computational complexity of the computer depending on the number of atoms, with only the minimum overhead of the CPU.

(4) Intermediate Representation Generating Process

The eigenvectors obtained through the above process have the directions of the principal axes of inertia, but are sorted in the order of the eigenvalues for the comparison of the coordinate systems. In this invention, the direction of the eigenvector v1 corresponding to the minimum eigenvalue is defined as the X axis, and the direction of the eigenvector having the next larger eigenvalue is defined as the Y axis. In this case, the direction of the Z axis is selected in the right hand coordinate system in the specific embodiment of the invention, but may be selected in the left hand coordinate system. Also, the database contains as sets of data, pieces of information as to the molecular structure including the coordinate values of atom, the interatomic distances between the remotest pair and the nearest pair, and the moments of inertia I1 to I6 in the Z matrix format or Cartesian format. The position of atom is projected onto the principal axes of inertia that is set up in the above way, whereby the positional coordinates of each atom projected onto the principal axes of inertia are calculated, paired or linked with the molecular structure, the interatomic distance between the remotest pair and the moment of inertia, and registered as the intermediate representation for the atomic arrangement generated from the atomic arrangement notation.

Figure 6:
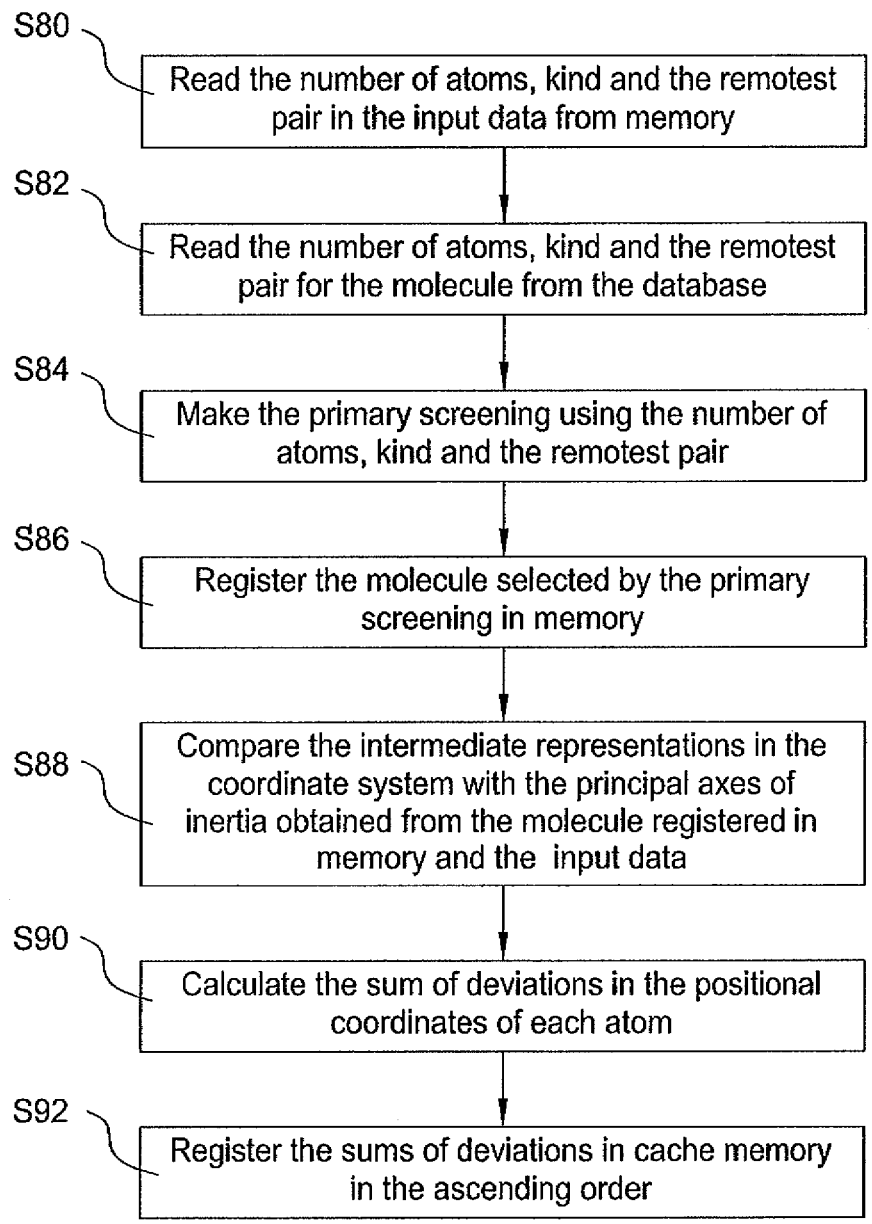
FIG. 6 is a flowchart of a retrieval process employing the intermediate representation of the invention.

FIG. 6 is a flowchart of a retrieval process performed by the retrieval executing part in the molecular information providing apparatus 18 as shown in FIG. 2. In this invention, the retrieval process is performed by the comparison with the intermediate representation generated through the above process. In the retrieval process performed by the retrieval executing part as shown in FIG. 6, at step S80, the number of atoms, the atomic attribute and the remotest pair in the input data are read out from the memory, and registered in an appropriate memory. Then, at step S82, they are compared with the number of atoms, the atomic attribute and the remotest pair for the molecule registered in the database. At step S84, the primary screening is performed, employing the number of atoms, the atomic attribute and the remotest pair. At step S86, the molecule extracted as a result of the primary screening is registered in a cache memory.

At step S88, the intermediate representation generated from the input data and the intermediate representation of the molecule registered in the cache memory are compared. Specifically, to make this comparison, the maximum value of positional deviation in the intermediate representation of each atom is calculated at step S90, and the maximum values are written in the smaller order into the cache memory at step S92, whereby the candidate molecule is chosen for the user. A secondary screening involves the steps S88 to S92 to improve the retrieval precision in this invention. In the secondary screening, the comparison is made at high precision, employing the intermediate representation in a coordinate system as seen from the principal axes of inertia, whereby the requested molecule is retrieved at high precision and the presence or absence of registering the molecule corresponding to the input atomic arrangement notation in the database can be rapidly and securely determined.

A comparing process including the primary screening and the secondary screening will be more particularly described. First of all, the data passing through the primary screening using the distance between the remotest pair, the number of atoms, and the kind of atom is registered in the cache memory or the like. In this case, if there are a plurality of the remotest pair candidates and a plurality of candidates for the atom farthest therefrom, but the total number of candidates is smaller, the secondary screen which will be described hereafter may be performed for all the combinations of candidates. Also, if the total number of candidates is great, the number of candidates is decreased by the symmetrical operation as used in the group theory, and the comparison is made only for remaining candidates.

The specific comparing process in the secondary screening will be further described below. It is assumed that the coordinate system for the intermediate representation of the molecule registered in the database is represented by XYZ, and the coordinate system for the intermediate representation of generated by a so-called query atomic arrangement caused from the atomic arrangement notation specified by the user is RST. In comparing the intermediate representations, it is firstly required to define a way of how the XYZ coordinate system and the RST coordinate system are superposed. There are a variety of methods for it, but a certain rule must be provided for the superposition of the coordinate systems, because the eigenvector is arbitrary in the sign. For the superposition of the coordinate systems, if Z and T are defined in the unified right hand system, there are four possible ways of (I) X and R, Y and S, (II) X and R, Y and –S, (III) X and –R, Y and S, and (IV) X and –R, Y and –S. For example, in the specific embodiment of the invention, four ways of superposition are compared for two atoms of the remotest pair, and a combination having the least sum of the absolute value (square mean) of residuals in the coordinate values of atom is selected. However, besides the above method, the superposition of the coordinate systems and the criterion for use in the judgment of coincidence may rely on any of the known methods.

Then, the corresponding atom is searched in this coordinate system, and the absolute values of residuals in the XYZ coordinate system and the RST coordinate system for the corresponding atom are calculated, whereby the maximum value of residual is notified as the coincidence criterion to the user. The user decides the molecular structure to be analyzed, and a determination is made whether or not it is consistent with the molecular structure in the database, employing this maximum value. This is based on the fact that the quality of input data by the user is unknown at the molecular information providing site, because there is the possibility that the precision of the interatomic distance and the dihedral angle in the atomic arrangement notation specified by the user, or the precision of the graphical user interface in generating the atomic arrangement notation is different for each data. Moreover, the analysis result at higher precision may be retrieved than the structure input by the user, and the user can utilize the analysis result stored in the database, irrespective of the residuals.

Figure 7:
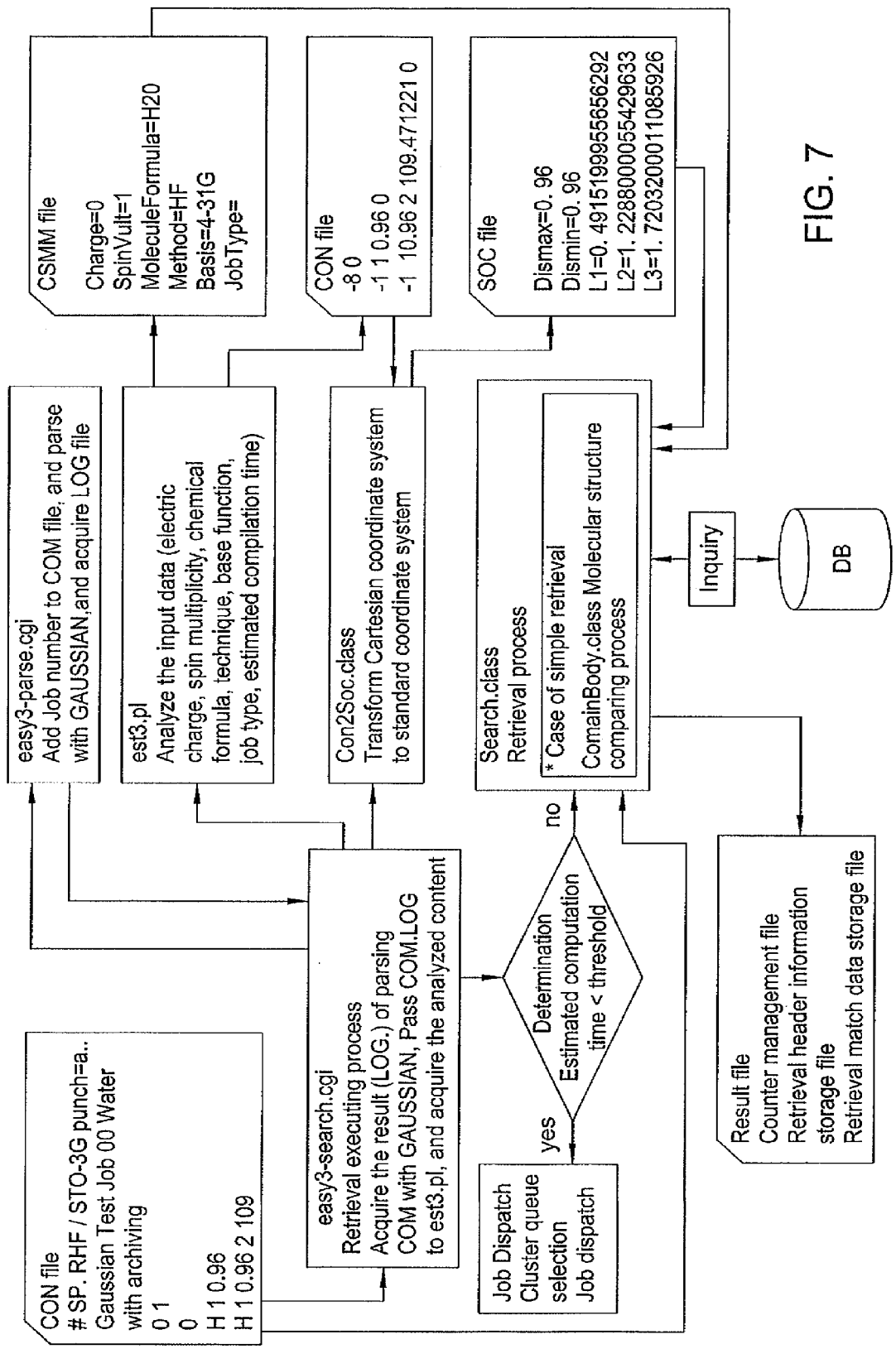
FIG. 7 is a diagram schematically showing a data structure and a data passing process that is used in a GAUSSIAN package software with a molecular information providing method of the invention.

FIG. 7 is a diagram schematically showing a process performed by the molecular information providing apparatus of the invention, along with the data structure for the process, employing a GAUSSIAN (trademark) as a program package for performing the analysis process. Naturally, when the program package for performing the analysis process is MOPAC, the program module is configured so that the same process may be performed in a different format of a file including the equivalent information. In FIG. 7, the file generated from the received user input data is indicated as a "COM file". Also, in the embodiment as shown in FIG. 7, the input molecule is indicated as H2O. Also, the data is described, specifying that the computation method is a non-empirical computation method RHF (Restricted Hartree Fock), the base function is STO-3G, the electric charge is O (neutral), and the spin multiplicity is singlet. The molecular structure is specified such that the O—H interval is 0.096 nm, and the H—O—H interval is 109°.

Figure 8:
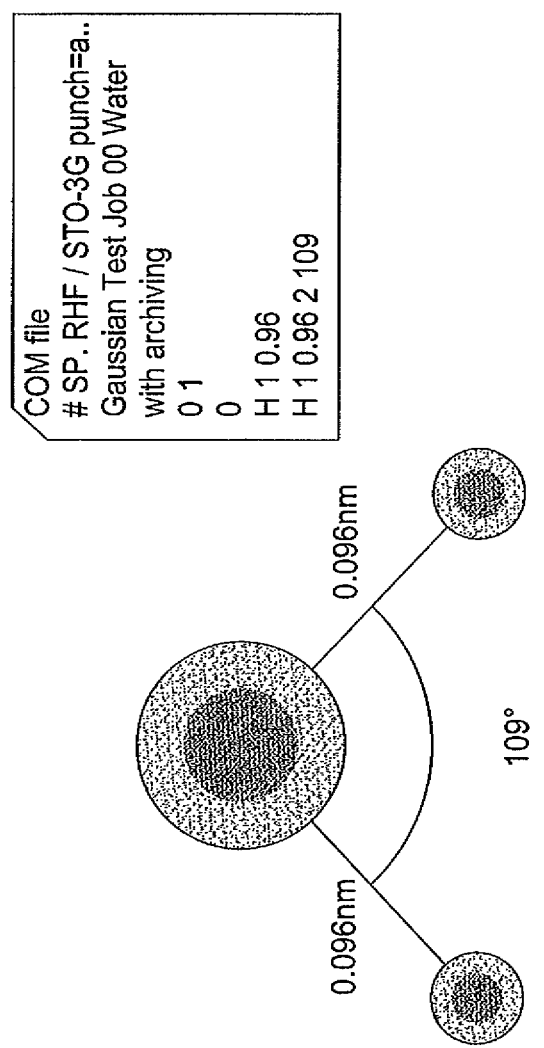
FIG. 8 is a view showing a structure of H2O molecule giving the data structure as shown in FIG. 7 and an atomic arrangement notation in the Z matrix format.

This COM file is analyzed by the input data analyzing part, whereby the information such as a LOG file for parse execution and the charge spin multiplicity is acquired as est3.pl to generate a CSMM file and a CON file. Moreover, information is transformed into the Cartesian coordinate system as Con2Soc.class and further the coordinate system for the intermediate representation, on the basis of the LOG file and the result of est3.pl. The intermediate representation data generated for H2O is indicated as an SOC File in FIG. 7. The estimated computation time generated with est3.pl is compared with a threshold value in a Determination process, and if it is shorter than the threshold time, the molecular orbital computation is performed in Job Dispatch. If it is longer than the threshold time, the retrieval process "Search.class" is performed, and the molecular structure comparing process using the intermediate representation is performed. In this case, the analysis result specified by the SOC file is linked with the information such as the CSMM file and the CON file, and provided as the retrieval information to the user. The retrieval process "Search.class" involves making an inquiry for the SOC file as query data to the database DB, and outputting the result of the primary screening and the secondary screening as a Result file to the memory to generate the retrieved result. FIG. 8 is a view showing a structure of H2O molecule that is employed in the process as shown in FIG. 7 and an atomic arrangement notation in the Z matrix format. As shown in FIG. 8, the molecule H2O does not degenerate in the moment of inertia and is processed by the molecular information providing method of the invention without problem.

Figure 9:
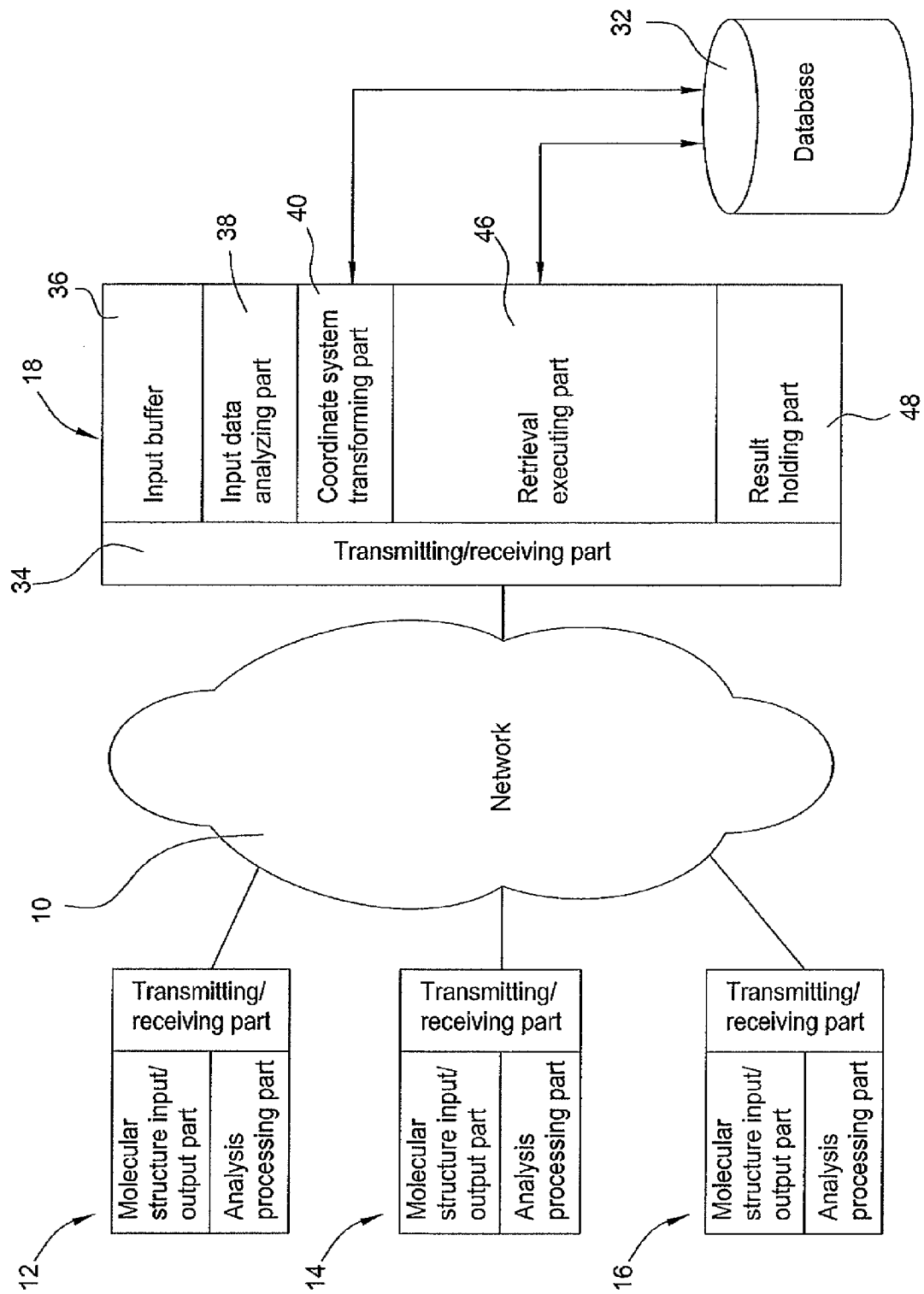
FIG. 9 is a diagram showing a molecular information providing system according to a second embodiment of the invention.

FIG. 9 is a block diagram showing a molecular information providing system according to a second embodiment of the invention. The molecular information providing system as shown in FIG. 9, like the molecular information providing system as shown in FIG. 1, is composed of the terminal units 12 to 16 interconnected via the network 10, and the molecular information providing apparatus 18 for receiving the coordinate information of molecule and the analysis result for the molecule by the molecular orbital computation from the terminal units 12 to 16 via the network 10 and performing the molecular orbital computation, as needed. The terminal units 12 to 16 consist of information processing means such as a workstation, a general-purpose large computer, or a personal computer in the same manner as in FIG. 1. The information processing apparatus for the terminal unit 12 to 16 has the hardware resources capable of performing the molecular orbital computation at fully high precision, and comprises Gaussian, MOPAC, or other molecular orbital computation package to execute the molecular orbital computation upon an instruction from the user.

Moreover, the molecular information providing apparatus 18 of the invention as shown in FIG. 9 comprises an information processing apparatus such as a workstation, a general-purpose computer or a so-called super computer, in which the past computation result stored in the database 32 is retrieved, employing the information transmitted from the terminal unit, and if the past analysis result is found, the information is transmitted to the terminal units. Also, the molecular information providing apparatus 18 according to the second embodiment of the invention as shown in FIG. 9 may operate as a center for sharing the analysis data computed by the terminal unit 12 to 16. That is, the terminal unit 12 to 16 transmits the analysis result of the molecular orbital computed by a computation method specified by the user, together with the information such as the atomic arrangement notation of molecule, the computation method and the computation conditions, to the molecular information providing apparatus 18.

The molecular information providing apparatus 18 receives from the terminal unit 12 to 16 the analysis result, the atomic arrangement notation, a designation of the method of molecular orbital computation, the base function, and the parameters necessary for the analysis, and stores the received information in the input buffer 36. The data including the analysis result and the atomic arrangement notation stored in the input buffer 36 is read into the input file analyzing part 38, in which the atomic arrangement notation format employed by the user is determined. The input file analyzing part 38 acquires the designation of the method of molecular orbital computation, the base function and the parameters necessary for the analysis on the basis of the data read from the input buffer 36. If the atomic arrangement notation format is determined in the input file analyzing part 38, the acquired atomic arrangement notation is passed to the coordinate system transforming part 40, and transformed into the intermediate representation, which is then registered in the database 32, along with the other information.

If receiving a retrieval request from the terminal unit, the molecular information providing apparatus 18 passes the intermediate representation generated in the coordinate system transforming part 40 to the retrieval executing part 46, makes an inquiry to the database, and stores the retrieved result in the result holding part 48. The retrieved result stored in the result holding part 48 is passed to the terminal unit issuing the retrieval request.

The molecular information providing apparatus 18 according to the second embodiment of the invention operates as a molecular information providing server to share among all the terminal units the result of molecular orbital computation computed in each terminal unit 12 to 16, without regard to a difference in the input format between the terminal units, even if it does not possess the capability of performing the molecular orbital computation by itself. The molecular information providing apparatus according to the second embodiment of the invention retrieves information in a general format in the large-scale computing environment of the molecular orbital computation, removes a waste of duplicate computing resources by performing the molecular orbital computation, and provides the efficient research development environment.

Figure 10:
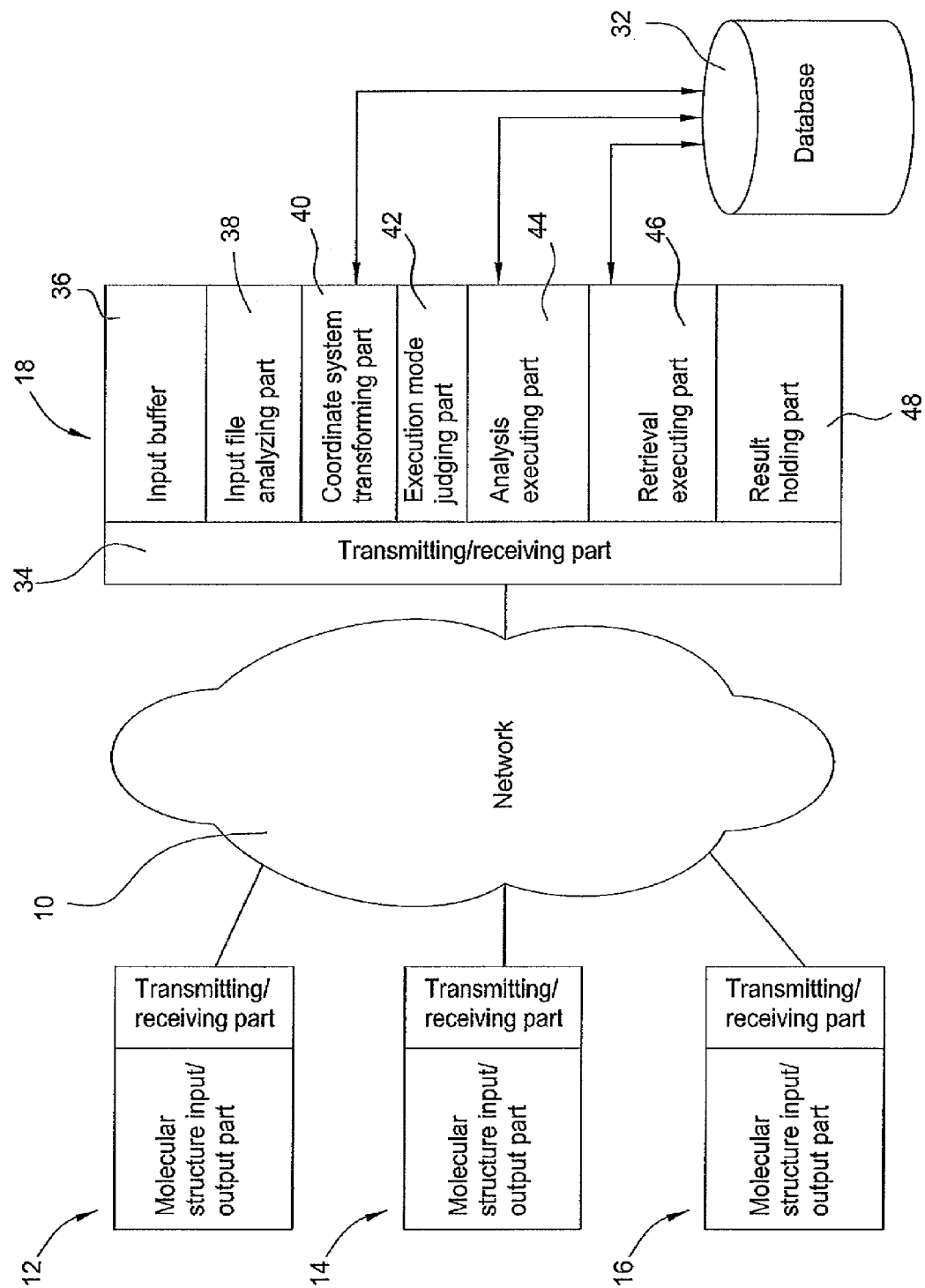
FIG. 10 is a diagram showing a molecular information providing system according to a third embodiment of the invention.

FIG. 10 is a block diagram showing a molecular information providing system according to a third embodiment of the invention. The functions of the molecular information providing apparatus 18 in the molecular information providing system as shown in FIG. 10 are the same as those of the molecular information providing apparatus as shown in FIG. 1, in which the molecular information providing apparatus 18 provides the analysis result accumulated in the database 32 upon a retrieval request from the terminal unit 12 to 16. In the molecular information providing system according to the third embodiment of the invention as shown in FIG. 10, the terminal unit 12 to 16 generates the molecular structure, employing the graphical user interface. The atomic arrangement notation obtained from the generated molecular structure is transmitted along with the retrieval or analysis result to the molecular information providing apparatus 18. The molecular information providing apparatus 18 performs the retrieval or analysis computation upon the request, and transmits its result to the terminal unit 12 to 16. The terminal unit 12 to 16 receives the result, and displays the result through the graphical user interface. In the third embodiment of the invention as shown in FIG. 10, the terminal unit is simplified in the installation, whereby it is possible to make the high precision retrieval for the information without regard to the input format of the terminal unit, and share the information with high added value at low cost.

EXAMPLES

Retrieval for molecular information employing the intermediate representation of this invention will be specifically described below by way of example, but the invention is not limited to those examples.

Example 1

Benzene (H6C6)

Figure 11:
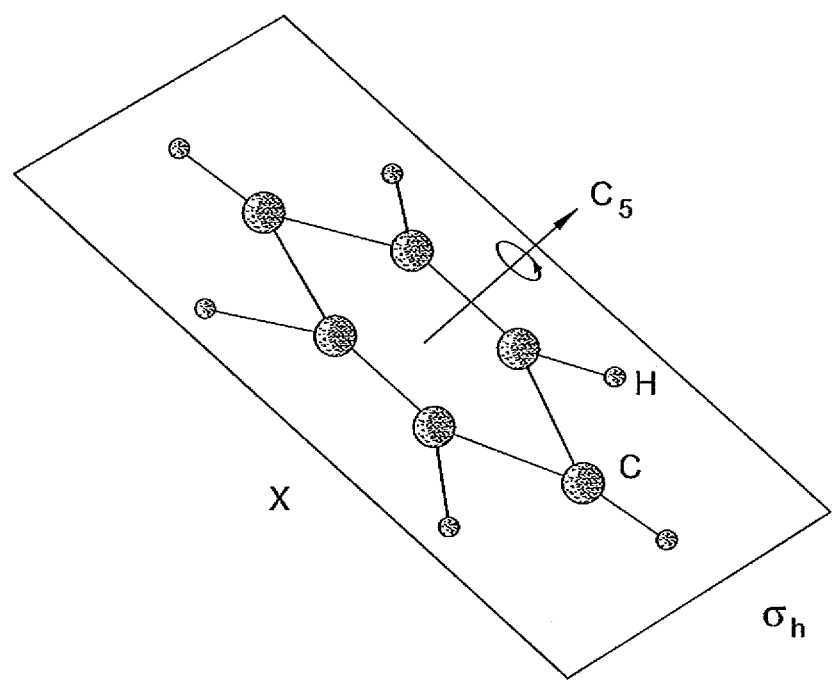
FIG. 11 is a view showing a molecular structure of benzene (C6H6) and the typical symmetrical elements.

FIG. 11 is a view showing a molecular structure of benzene (C6H6). Benzene C6H6 is a fundamental molecule composed of six carbon atoms and six hydrogen atoms, or a total of twelve atoms. However, benzene has a high symmetry D6h, in which a plane of reflection sh and a C6 axis perpendicular to the plane of reflection sh are defined in FIG. 11. Besides, for benzene, a plane of reflection sv containing the C6 axis may be defined, but is not shown in FIG. 11. To give an atomic arrangement notation in the Z matrix format described later, a dummy atom X (not included in the computation) is shown, in which the positions of C atom and H atom are defined by the distance from X and the dihedral angle.

Figure 12:
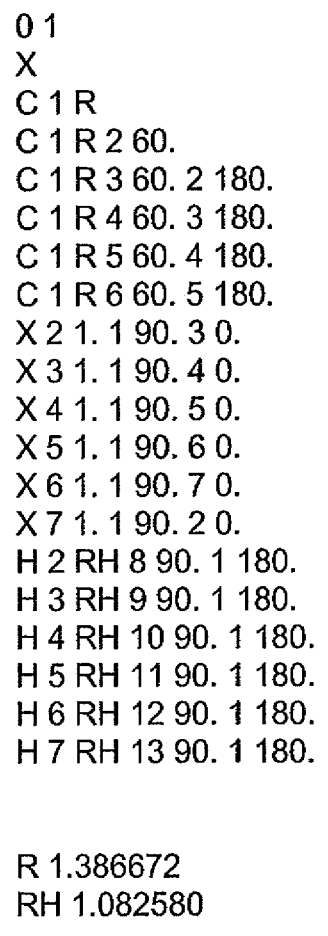

FIG. 12 shows an atomic arrangement notation of benzene C6H6 in the Z matrix format. The Z matrix format has the atomic symbols in the first column, and to the right, the reference atom, the bond length between the reference atom and its atom (hereinafter the bond length is given in a unit of Œ in the atomic arrangement notation of this invention), second reference atom, bond angle (degrees) with the second reference atom, third reference atom, and dihedral angle with the third reference atom, whereby the relative positional relation between atoms is defined. The bond length R, RH and the angle may be directly input by numerical values, or via the variables. In the example as shown in FIG. 12, the bond length is defined by the variables R and RH. The molecular structure input by this method is transformed into the Cartesian coordinate system inside the GAUSSIAN and utilized for the molecular orbital computation.

In this invention, employing the Cartesian coordinates obtained from the atomic arrangement notation described above, an inertial matrix is generated, assuming that C has a mass of 6, H has a mass of 1, and X is a rigid body having a mass of 0. A benzene ring is a regular hexagon, whereby two principal moments of inertia orthogonal to the C6 axis have considerably near values according to the multiple root or rounded precision. The eigenvalues of the inertial matrix were calculated for the benzene molecule with the atomic arrangement notation in the Z matrix format, using a personal computer, so that the principal moments of inertia for benzene had the multiple root given by the following formulas.

$$I1=I2=52.9031, I3=105.8062 \qquad \text{Formula 1}$$

In benzene, the remotest pair is two H atoms as shown in FIG. 11. Thus, according to the invention, the proximate eigenvalue handling process was performed to calculate the eigenvalues again for the same point sequence arrangement by selecting one H at the position farthest away from the remotest pair, and increasing its mass by four times, assuming that the mass of H atoms in the remotest pair is 8. As a result, the eigenvalues are shown for the moments of inertia in the following formula 2. As indicated in the following formula 2, it will be found that the degeneration in the moment of inertia or the eigenvalue is resolved.

$$I4=65.1941, I5=143.334, I6=208.528 \qquad \text{Formula 2}$$

Assuming that the eigenvectors v4 and v5 corresponding to those eigenvalues have the X and Y directions, respectively, the Z direction being defined in the right hand system, the positions of all the atoms are transformed into the coordinate system for the intermediate representation, whereby the molecular structure on the retrieved side is created and registered in the memory.

Thereafter, the intermediate representation of molecule registered in the database was generated by simulation. In the simulation, the molecular structure on the retrieving side was generated in the intermediate representation from the atomic arrangement notation in the Cartesian coordinate system of GAUSSIAN. To simulate the GAUSSIAN, the atomic arrangement notation in the Z matrix format as shown in FIG. 12 was transformed into the Cartesian coordinate system, and the atomic arrangement notation on the retrieved side was created by rounding off at the sixth decimal place. Its result is shown in FIG. 13. The atomic arrangement notation as shown in FIG. 13 represents a regular hexagon with significant five digits accurately.

The precision of the atomic arrangement notation as shown in FIG. 13 was examined by checking the position of C, whereby the multiple root was not correctly obtained due to the influence of numerical round-off. The eigenvalues for the inertial matrix on the retrieved side are given in the following formula 3.

$$I1=52.9028, I2=52.9032, I3=105.8059 \qquad \text{Formula 3}$$

Figure 14:
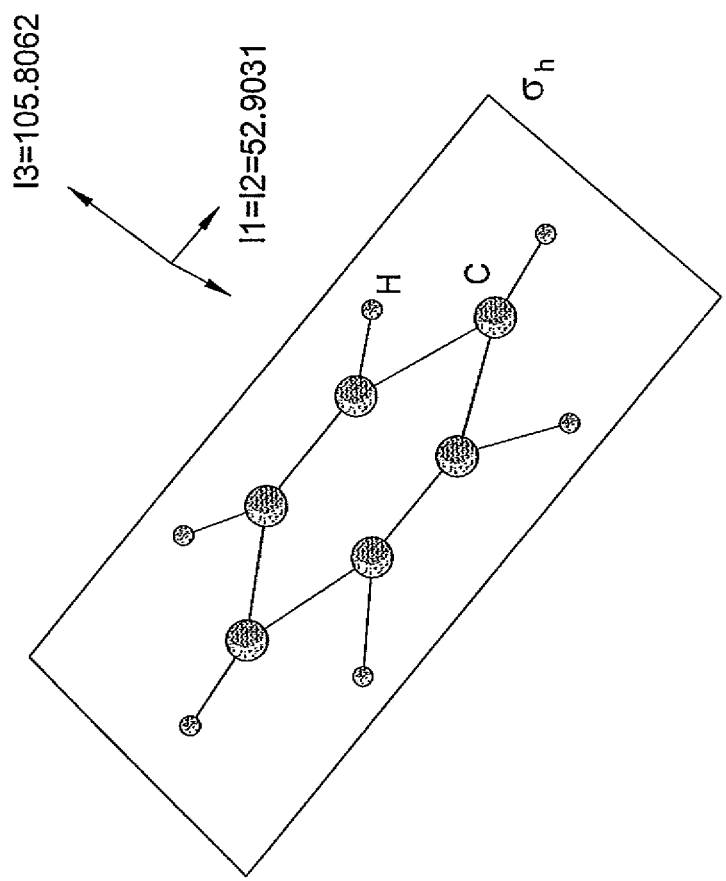
FIG. 14 is a view showing a moment of inertia with a principal axis of inertia computed as an eigenvalue of an inertial matrix for benzene without applying this invention.
Figure 15:
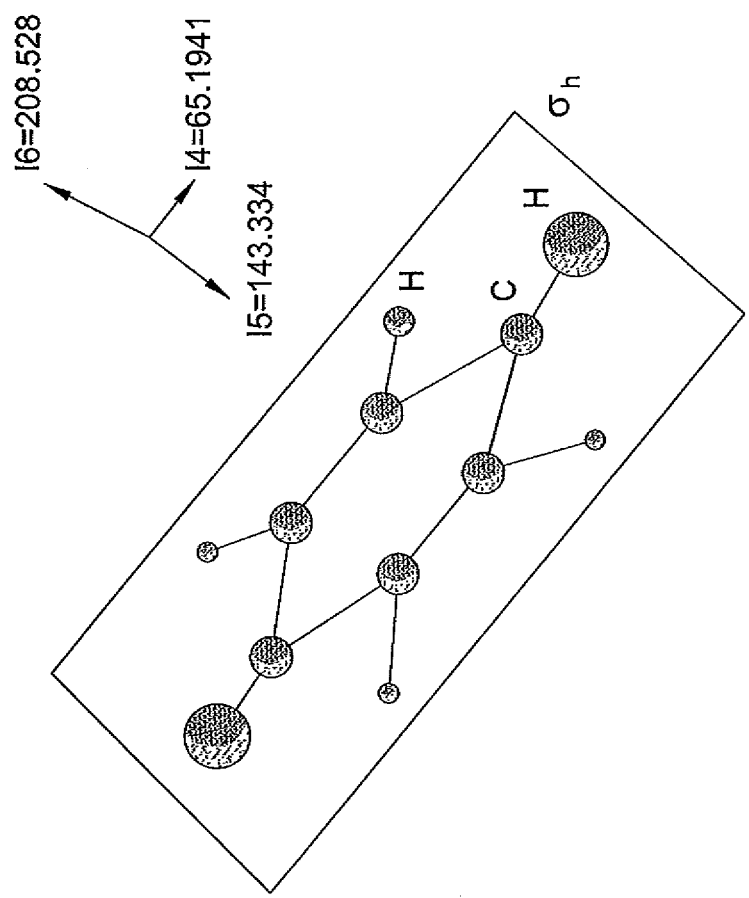
FIG. 15 is a view showing the structure of a virtual molecule for benzene generated through a proximate eigenvalue handling process according to this invention.

FIG. 14 is a view showing the obtained moments of inertia and the directions of the principal axes of inertia. As shown in FIG. 14, I1 and I2 are proximate on the retrieved side. Thus, according to the invention, the proximate eigenvalue handling process was performed, whereby an inertia matrix was created by increasing the mass of H atoms in the remotest pair by eight times and increasing the mass of H atom farthest away from the remotest pair by four times, and registered in the memory. Then, the eigenvalue computation was performed again. FIG. 15 shows conceptually the proximate eigenvalue handling process of the invention. In FIG. 15, the size of atom substantially corresponds to the multiplier by which the mass is multiplied. As shown in FIG. 15, there are four candidates for H atom farthest away from the line of the remotest pair. Thus, the computation on the retrieved side was made for all the four candidates for H atom at the farthest position to judge the precision. As a result, the eigenvalues (i.e., moments of inertia) in the intermediate representation were obtained as the moments of inertial having the values as shown in the following formula, without regard to the position of H atom.

$$I4=65.1938, I5=143.334, I6=208.528 \qquad \text{Formula 4}$$

The coordinate system is obtained from the corresponding eigenvectors in four combinations depending on whether the R direction is I4 or −I4 direction, and the S direction is I5 or −I5 direction. Herein, the T direction is automatically defined in the right hand system, if the R direction and the S direction are decided. In the example of benzene as shown in FIG. 15, the T direction was appropriately selected only by comparing a degree of superimposition of the atoms of the remotest pair on the retrieved side and those on the retrieving side.

Employing the coordinate values for the intermediate representation obtained in the above manner, the positions of all the atoms were compared for each atom to calculate the residuals in both the molecular structures and register them in the memory. As the final output, the four different ways of the farthest atom were selected, and for the atom having the minimum sum of the absolute value (coincidence criterion) of residuals in the positional coordinates of atoms, the absolute value (coincidence criterion) of the maximum residual in comparing the atom positions was stored in the memory, along with the distance between the remotest pair and the nearest pair, and the content of memory was output. Its result is shown in Table 1.

TABLE 1

Maximum residual = 0.00000711
Remotest pair = 4.94
Nearest pair = 1.08

Example 2

Examining the Effect of Significant Digits (H6C6)

The stability and dependency of the molecular structure on the retrieving side on the number of digits in the coordinate values were examined by reducing the significant digits in the atomic arrangement notation on the retrieving side down to the third decimal place. As the input data, the atomic arrangement notation as shown in FIG. 16 was employed. Table 2 shows the eigenvalues calculated from the atomic arrangement notation as shown in FIG. 16. There are four candidates for H atom farthest away from the remotest pair, but due to a slight difference between eigenvalues in the atomic arrangement notation as shown in FIG. 16, two ways of result were obtained. The masses of hydrogen atoms in the remotest pair and the mass of hydrogen atom farthest away from the remotest pair were increased by eight times and four times, respectively.

TABLE 2

I1 = 52.9018, I2 = 52.9040, I3 = 105.8058
I4 = 65.1883, I5 = 143.3233, I6 = 208.5116
I4 = 65.2000, I5 = 143.3124, I6 = 208.5125

The intermediate representation was created employing the principal axes of inertia, and the residuals of the atom positions on the retrieving side and the retrieved side in the example 1 were calculated. The maximum value (coincidence criterion) of the absolute value of residual was equal to 0.0012, indicating that there was a sufficient coincidence in the order of significant digits. That is, the significant digits of the coordinate values in the input data, the number of digits consistent in the eigenvalues, and the maximum value of residual finally obtained are correlated, and the precision of the input data produced by the user can be judged using this value as the coincidence criterion. Therefore, the user can retrieve the database using this information, and at the same time, find the retrieval result at high precision.

Example 3

Furaren (C60)

Figure 17:
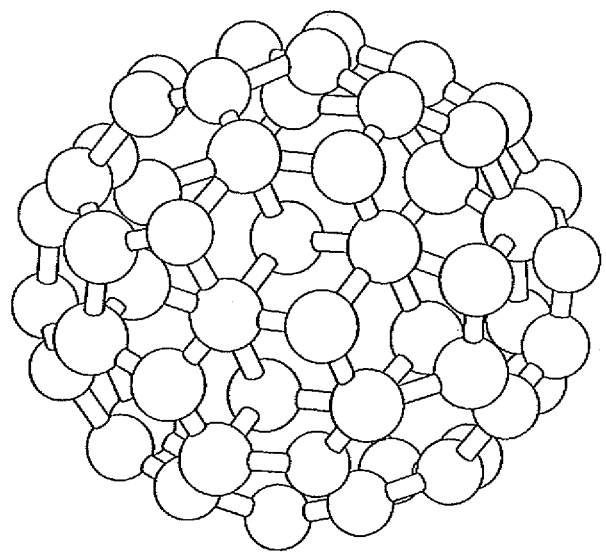
FIG. 17 is a view showing a molecular structure of C60 generated through the use of a graphical user interface.

This invention was applied to furaren having 60 carbons which are bonded spheroidally. A molecular structure of C60 was created employing the graphical user interface, and the atom positions were optimized by the molecular dynamic method. FIG. 17 shows the optimized structure of C60. An atomic arrangement notation of furaren in the Cartesian format was produced from the atomic arrangement obtained in this way, and rounded off to the seventh significant digit to produce the data on the retrieved side.

Three eigenvalues of the inertial matrix were proximate owing to the symmetrical structure of furaren, and the following moments of inertia as shown in Formula 5 were obtained in the example 3.

$$I1=2913.89019, I2=2933.06738, I3=2935.7008 \quad \text{Formula 5}$$

In the example 3, a difference between I2 and I3 was about 0.1% and I2 and I3 were the proximate eigenvalues. This invention was applied to furaren, in which the principal axes of inertia were produced by increasing the masses of C atoms in the remotest pair by eight times, and the mass of C atom farthest away from the remotest pair by four times, so that the following three eigenvalues were obtained.

$$I4=3125.56966, I5=4012.94784, I6=4224.8405 \quad \text{Formula 6}$$

Furaren C60 having the above structure was rotated, the origin was moved to vary the atomic coordinates, the atomic arrangement notation having the seven significant digits was created in the Cartesian format, the data on the retrieving side was produced, and the maximum value (coincidence criterion) of residual in the atoms, the distance between the remotest pair, and the distance between the nearest pair was calculated in the same manner as in the example 1. Its result is shown in Table 3. As shown in Table 3, the maximum difference in the order of significant digits is obtained, indicating the excellent index.

TABLE 3

Maximum residual = 0.0000016
Remotest pair = 7.17
Nearest pair = 1.18

Example 4

Examining the Significant Digits (C60)

The same examination of the example 3 was performed by increasing the significant digits of the input atomic arrangement notation on the retrieving side up to the ninth decimal place, whereby the maximum difference was 0.0000000093. Also, by decreasing the significant digits of the input atomic arrangement notation down to the fourth decimal place, the maximum difference was 0.0000096, indicating that the maximum difference was an excellent index.

Example 5

Aerial Molecule (Be2O2S2)

Figure 18:
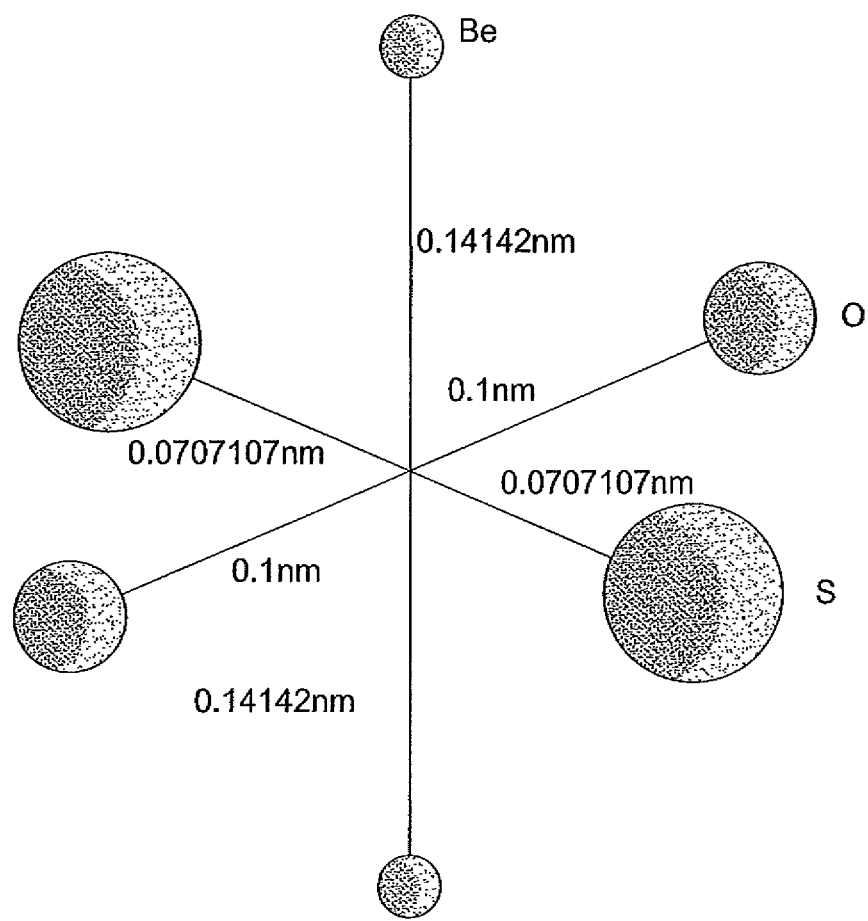
FIG. 18 is a view showing the structure of a virtual molecule Be2O2S2.

Moreover, to examine the effect of the invention, an aerial molecule having the proximate moments of inertia in connection with the mass of atom was employed, though the moments of inertia are not multiple root in the structure. Table 4 shows the atomic arrangement notation of the aerial molecule (the bond length is given in a unit of OE and the angle is in a unit of degree (°)). FIG. 18 shows the structure of the aerial molecule.

TABLE 4

O 1. 0. 0.
O −1. 0. 0.
Be 0. 0. 1.4142
Be 0. 0. −1.4142
S 0. 0.707107 0.
S 0. −.707107 0.

The atomic number of O is 8, the atomic number of Be is 4, and the atomic number of S is 16. Accordingly, when O is placed at 1 and −1 on the X axis, two atoms of Be placed at its SQRT(2) times distance have the effect with the equivalent moments of inertia, and atom S placed at the 1/SQRT(2) times distance has also the same effect. Though this aerial molecule does not have triple root from the symmetry and the coordinate values, the eigenvalues of the inertial matrix give the proximate roots, I1=31.99969, I2=31.99970, and I3=32.0000099. On the contrary, if the masses of atoms in the remotest pair are increased by eight times, and the mass of O atom is increased by four times, the following moments of inertia result.

$$I4=51.7647, I5=143.998, I6=163.7622 \quad \text{Formula 7}$$

As described above, in this invention, a stable comparison is made without numerical uncertainty in judgment for the principal axes of inertia. As shown in the example 5, in this invention, no multiple root appears from the coordinate values of atoms, whereas the problem is made numerically stable easily and rapidly only by "updating the inertial matrix to solve the eigenvalue problem of 3'3 matrix again", after actually determining the existence of multiple root, although the user does not predict that the moments of inertia are proximate, namely, the increased computation time due to existence of multiple root does not depend on the number of atoms to be retrieved, whereby the retrieval is efficiently made at high precision.

Means or part for implementing each function of the invention as above may be configured as a software or a group of software modules described in a computer executable programming language, but is not necessarily required to be configured as a functional block described on the drawings.

The program for performing the molecular information providing method of the invention is described in various programming languages, for example, C language, C++ language, JavaO and Fortran, and the code describing the program of the invention is stored in a computer readable recording medium, such as a magnetic tape, a flexible disk, a hard disk, a compact disk (CD), an optical magnetic disk, or a digital versatile disk (DVD).

As described above, with this invention, the detectability for the molecule having the same structure is enhanced, and the high precision retrieval is enabled without depending on the format employed by the user, whereby the molecular information providing system capable of sharing the data of molecular orbital computation is provided.

Nowadays, the scientific and technical computation has begun to transfer to a grid computing environment of large-scale numerical computation simulation worldwide. The molecular orbital method is one of the applications consuming the greatest amount of computation time in this field. For example, a molecule of amino acid having a large number of atoms takes a few days for computation in many cases. Therefore, the GAUSSIAN grid is easy to exhibit the effects of grid computing as seen from the operating side of the grid computing. If a plurality of GAUSSIAN grids start to operate, the contention of molecular orbital computation is foreseen, whereby it is necessary to realize the efficient operation of computer resources. This invention is implemented on the above portal routine to increase the hit rate in the database. Though this invention has been described using the GAUSSIAN as a software package for performing the molecular orbital computation, this invention is easily extended to other molecular orbital applications than the GAUSSIAN. For example, this invention is applicable to MOPAC and GAMESS (www.msg.ameslab.gov/GAMESS/GAMESS.html) having many functionally duplicate portions, in which by analyzing the atomic arrangement notation of GAMESS and retrieving the database of MOPAC, GAMESS and GAUSSIAN transversely, the user may be responded with the information "there is the computation result of GAUSSIAN".

While the foregoing is directed to embodiments of the present invention, other and further embodiments of the invention may be devised without departing from the basic scope thereof, and the scope thereof is determined by the claims that follow.

| [Description of symbols] | |
|---|---|
| 10 | Network |
| 12, 14, 16 | Terminal units |
| 18 | Molecular information providing apparatus |
| 20 | Molecular structure input/output part |
| 22 | Analysis executing part |
| 24 | Transmitting/receiving part |

-continued

| [Description of symbols] | |
|---|---|
| 26 to 30 | User databases (user DBs) |
| 32 | Database |
| 34 | Transmitting/receiving part |
| 36 | Input buffer |
| 38 | Input file analyzing part |
| 40 | Coordinate system transforming part |
| 42 | Execution mode judging part |
| 44 | Analysis executing part |
| 46 | Retrieval executing part |
| 48 | Result holding part |
| 50 | Memory |
| 52 | Fast access memory |

The invention claimed is:

1. A computer readable storage medium containing an executable program for controlling a molecular information providing apparatus that is an information processing unit including a database for retrieving a characteristic decided depending on a molecular structure on a basis of said molecular structure, said program being executed by said information processing unit, where the program performs steps comprising:

calculating principal axes of inertia from an atomic arrangement notation specifying said molecular structure;

registering said principal axes of inertia in a memory;

determining how close a principal moment of inertia of said molecular structure is to said principal axes of inertia;

reading out data of the principal axes of inertia from said memory;

registering in said database an intermediate representation that is a coordinate transformation of atomic coordinates of said molecular structure into a coordinate system in directions of said principal axes of inertia;

computing a molecular orbital corresponding to said molecular structure, when an estimated computation time for said computing does not exceed a threshold value;

retrieving the molecular structure from said database, employing said intermediate representation, when said estimated computation time exceeds said threshold value; and registering the molecular structure, as retrieved, in the memory.

2. The program according to claim 1, wherein calculating the principal axes of inertia comprises:

changing a first atomic attribute of atoms making up a remotest pair in the molecular structure and a second atomic attribute of an atom farthest away from the remotest pair.

3. The program according to claim 1, wherein said method further comprises:

calculating a characteristic decided depending on said molecular structure, wherein the characteristic decided depending on said molecular structure is given by a molecular orbital computation and is an electronic characteristic of a molecule, an electrical characteristic of a molecule, or an optical characteristic of a molecule.

* * * * *